US006284266B1

(12) United States Patent
Zhang et al.

(10) Patent No.: US 6,284,266 B1
(45) Date of Patent: *Sep. 4, 2001

(54) METHODS AND APPARATUS FOR IMPROVED ADMINISTRATION OF FENTANYL AND SUFENTANIL

(75) Inventors: Jie Zhang; Hao Zhang, both of Salt Lake City, UT (US)

(73) Assignee: Zars, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/162,587

(22) Filed: Sep. 29, 1998

(51) Int. Cl.$^7$ .................................................. A61K 9/70
(52) U.S. Cl. ..................... 424/449; 424/448; 424/447; 424/443; 424/402; 602/41; 602/46
(58) Field of Search .................... 424/402, 443, 424/447, 448, 449; 602/41, 46

(56) References Cited

U.S. PATENT DOCUMENTS

| | | | |
|---|---|---|---|
| D. 403,778 | 1/1999 | Davis et al. | D24/206 |
| D. 403,779 | 1/1999 | Davis et al. | D24/206 |
| D. 407,822 | 4/1999 | Davis et al. | D24/206 |
| D. 407,824 | 4/1999 | Davis et al. | D24/206 |
| D. 408,923 | 4/1999 | Davis et al. | D24/206 |
| D. 409,757 | 5/1999 | Davis et al. | D24/206 |
| D. 412,751 | 8/1999 | Davis et al. | D24/206 |
| D. 417,283 | 11/1999 | Davis et al. | D24/206 |
| D. 418,606 | 1/2000 | Davis et al. | D24/206 |
| 3,929,131 | 12/1975 | Hardwick . | |
| 4,210,670 | 7/1980 | Cooke | 424/324 |
| 4,230,105 | 10/1980 | Harwood . | |
| 4,286,592 | 9/1981 | Chandrasekaran . | |
| 4,529,601 | 7/1985 | Broberg | 514/626 |
| 4,685,911 | 8/1987 | Konno et al. . | |
| 4,693,706 | 9/1987 | Ennis, III . | |
| 4,747,841 | 5/1988 | Kuratomi et al. . | |
| 4,830,855 | 5/1989 | Stewart . | |
| 4,898,592 | 2/1990 | Latzke et al. . | |
| 4,911,707 | 3/1990 | Heiber et al. . | |
| 4,913,957 | 4/1990 | Strack et al. . | |

(List continued on next page.)

FOREIGN PATENT DOCUMENTS

| | | |
|---|---|---|
| 2 163 956 A | 3/1988 | (GB) . |
| WO 88/09169 | 12/1988 | (WO) . |
| WO97/01310 | 1/1997 | (WO) . |
| WO97/01311 | 1/1997 | (WO) . |
| WO97/01312 | 1/1997 | (WO) . |
| WO97/01313 | 1/1997 | (WO) |

(List continued on next page.)

OTHER PUBLICATIONS

"Room Temperature," MacMillan, U.S.A., *Webster's New World College Dictionary*, Third Edition, 1997, p. 1165.
Florey, Klaus, *Analytical Profiles of Drug Substances*, vol. 15, 1986, pp. 150–231.
Florey, Klaus, *Analytical Profiles of Drug Substances*, vol. 12, 1983, pp. 73–105.
"Local Anesthetics, Parenteral, General Statement," *AHFS Drug Information*, 1992.
Florey, Klaus, *Analytical Profiles of Drug Substances*, vol. 18, 1989, pp. 379–411.

(List continued on next page.)

*Primary Examiner*—Michael A. Williamson
(74) *Attorney, Agent, or Firm*—Kirton & McConkie; Michael F. Krieger

(57) ABSTRACT

Methods and apparatus for improving administration of analgesics through the use of heat. The present invention relates to the use of heat in conjunction with specially designed transdermal analgesic delivery systems and conventional commercial transdermal analgesic delivery systems to alter, mainly increase, the analgesic release rate from the transdermal analgesic delivery systems or the depot sites to accommodate certain clinical needs.

12 Claims, 24 Drawing Sheets

U.S. PATENT DOCUMENTS

| | | |
|---|---|---|
| 4,963,360 | 10/1990 | Argaud .................................. 424/443 |
| 4,994,049 | 2/1991 | Latzke et al. . |
| 5,108,710 | 4/1992 | Little et al. . |
| 5,114,411 | 5/1992 | Haber et al. . |
| 5,128,137 | 7/1992 | Müller et al ................................. . . |
| 5,147,339 | 9/1992 | Sundström . |
| 5,213,129 | 5/1993 | Someah et al. . |
| 5,217,718 | 6/1993 | Colley et al. . |
| 5,229,133 | 7/1993 | Wright et al. . |
| 5,276,032 | 1/1994 | King et al. . |
| 5,279,594 | 1/1994 | Jackson . |
| 5,329,976 | 7/1994 | Haber et al. . |
| 5,330,452 | 7/1994 | Zook . |
| 5,364,350 | 11/1994 | Dittman . |
| 5,534,021 | 7/1996 | Dvoretzky et al. ................... 607/112 |
| 5,580,573 | 12/1996 | Kydonieus et al. ................. 424/449 |
| 5,605,536 | 2/1997 | Sibalis .................................... 604/20 |
| 5,626,571 | 5/1997 | Young et al. ......................... 604/370 |
| 5,651,768 | 7/1997 | Sibalis .................................... 604/20 |
| 5,658,583 | 8/1997 | Zhang et al. .......................... 424/402 |
| 5,662,624 | 9/1997 | Sundstrom et al. .................. 604/291 |
| 5,728,057 | 3/1998 | Ouellette et al. ...................... 602/62 |
| 5,728,058 | 3/1998 | Ouellette et al. ...................... 602/62 |
| 5,728,146 | 3/1998 | Burkett et al. ....................... 607/109 |
| 5,733,255 | 3/1998 | Dinh et al. ............................. 604/20 |
| 5,735,889 | 4/1998 | Burkett et al. ......................... 607/96 |
| 5,741,318 | 4/1998 | Ouellette et al. ..................... 607/108 |
| 5,837,005 | 11/1998 | Viltro et al. .......................... 607/112 |
| 5,860,945 | 1/1999 | Cramer et al. .......................... 602/62 |
| 5,904,710 | 5/1999 | Davis et al. .......................... 607/108 |
| 5,906,637 | 5/1999 | Davis et al. .......................... 607/108 |
| 5,906,830 | 5/1999 | Farinas et al. ....................... 424/448 |
| 5,919,479 | 7/1999 | Zhang et al. ......................... 424/449 |
| 5,925,072 | 7/1999 | Cramer et al. ....................... 607/108 |
| 5,980,562 | 11/1999 | Ouellette et al. ..................... 607/108 |
| 5,984,995 | 11/1999 | White ...................................... 75/230 |
| 6,019,782 | 2/2000 | Davis et al. ............................ 607/96 |
| 6,020,040 | 2/2000 | Cramer et al. ....................... 428/64.1 |
| 6,024,761 | 2/2000 | Barone et al. ....................... 607/108 |
| 6,042,673 | 3/2000 | Johnson et al. ...................... 156/227 |
| 6,048,326 | 4/2000 | Davis et al. ............................. 602/ 6 |

FOREIGN PATENT DOCUMENTS

| | | |
|---|---|---|
| WO97/36968 | 10/1997 | (WO) . |
| WO97/49361 | 12/1997 | (WO) . |
| WO98/28021 | 7/1998 | (WO) . |
| WO98/28024 | 7/1998 | (WO) . |
| WO98/29063 | 7/1998 | (WO) . |
| WO98/29064 | 7/1998 | (WO) . |
| WO98/29065 | 7/1998 | (WO) . |
| WO98/29066 | 7/1998 | (WO) . |
| WO98/29067 | 7/1998 | (WO) . |
| WO99/09917 | 3/1999 | (WO) . |
| WO99/09918 | 3/1999 | (WO) . |

OTHER PUBLICATIONS

Sakamoto et al., "Dermal patch anesthesia: comparison of 10% lignocaine gel with absorption promoter and EMLA cream," *Anesthesia*, (1993), vol. 48, pp. 390–392.

Dvoretzky, Israel, M.D., Hyperthermia Therapy for Warts Utilizing a Self–administered Exothermic Patch, *Dermal Surgery*, (1996), vol. 22, pp. 1035–1039.

Stern, Peter, M.D. and Levine, Norman, M.D., "Controlled Localized Heat Therapy in Cutaneous Warts," *Arch. Dermatol*, (Jul. 1992), vol. 128, pp. 945–948.

Arky, et al., *Physicians' Desk Reference*, 1997, pp. 1336–1340.

Mack Publishing Company, "Stability of Pharmaceutical Products", *Pharmaceutical Sciences*, pp. 1481–1482, 1985.

McCafferty, et al., "Comparative In Vivo and In Vitro Assessment of the Percutaneous Absorption of Local Anaesthetics", *Br. J. Anaesth.*, vol. 60, (1988), 64–69.

Woolfson, et al., "Concentration Response Analysis of Percutaneous Local Anaesthetic Formulations" *Br. J. Anaesth.*, vol. 61, (1988), pp. 590–592.

McCafferty, et al., "In Vivo Assessment of Percutaneous Local Anaesthetic Preparations", *Br. J. Anaesth.*, vol. 62, (1989), pp. 18–21.

Knutson, et al., "Solvent–Mediated Alterations of the Stratum Corneum", *Journal of Controlled Release*, vol. 11, (1990), pp. 93–103.

Lycka, "EMLA, A New and Effective Topical Anesthetic", *J. Dermotol. Surg. Oncol.*, 18:859–862 (1992).

McCafferty, et al., "New Patch Delivery System for Percutaneous Local Anaesthesia", *Br. J. Anaesth.*, 71:370–374 (1993).

Woolfson, *Percutaneous Local Anaesthesia*, (1993), pp. 166–170.

Astra USA, Inc., "EMLA Cream Product Information Form For American Hospital Formulary Service", (1993), pp. 1–28.

METHODS AND APPARATUS FOR IMPROVED ADMINISTRATION OF FENTANYL AND SUFENTANIL

BACKGROUND OF THE INVENTION

1. Field of the Invention

The present invention relates to methods and apparatus for administration of fentanyl and sufentanil. More particularly, the present invention relates to using controlled heat to improve administration of fentanyl and sufentanil.

2. State of the Art

The dermal administration of pharmaceutically active compounds involves the direct application of a pharmaceutically active formulation(s) to the skin, wherein the skin absorbs a portion of the pharmaceutically active compound which is then taken up by the blood stream. Such administration has long been known in the practice of medicine and continues to be an important technique in the delivery of pharmaceutically active compounds. For example, U.S. Pat. No. 4,286,592 issued Sep. 1, 1981 to Chandrasekaran shows a bandage for administering drugs to a user's skin consisting of an impermeable backing layer, a drug reservoir layer composed of a drug and a carrier, and a contact adhesive layer by which the bandage is affixed to the skin.

Such dermal administration offers many important advantages over other delivery techniques, such as injection, oral tablets and capsules. These advantages include being non-invasive (thus, less risk of infection), avoiding first pass metabolism (metabolism of the drug in the liver when the drug is taken orally and absorbed through the gastrointestinal tract), and avoiding of high peaks and low valleys of concentration of pharmaceutically active compounds in a patient's bloodstream. In particular, high peaks and low valleys of concentration are typical in injection and oral administrations and are often associated with undesirable side effects and/or less than satisfactory intended effects.

The term "transdermal analgesic delivery system" or "TADS", as used herein, is defined as an article or apparatus containing analgesic(s) for delivery into the skin, the regional tissues under the skin, the systemic circulation, or other targeting site(s) in a human body via skin permeation. The term "TADS" in this application, unless otherwise specified, only refer to those systems in which the main driving force for drug permeation is the drug concentration gradient.

The term "analgesic", as used herein, is defined to include any pharmaceutically active compound which renders a human body or portion of a human body insensible to pain without loss of consciousness.

The term "skin", as used herein, is defined to include stratum corneum covered skin and mucosal membranes.

The term "clinical effect", as used herein, is defined to include at least a diminishing of pain in an individual patient. The amount of analgesic necessary for a clinical effect will, of course, vary from patient to patient.

In TADSs, an analgesic(s) is usually contained in a formulation, such as a hydro-alcoholic gel, and may include a rate limiting membrane between the formulation and skin for minimizing the variation in the permeation of the analgesic. When a TADS is applied to skin, the analgesic begins to transport out of the formulation, and transport across the rate limiting membrane (if present). The analgesic then enters the skin, enters blood vessels and tissues under the skin, and is taken into the systemic circulation of the body by the blood. At least some TADSs have certain amount of analgesic in or on the skin side of the rate limiting membrane (if present) prior to use. In those TADSs, that portion of the analgesic on the skin side of the rate limiting membrane will enter the skin without passing through the rate limiting membrane. A significant portion of the dermally absorbed analgesic may be stored in the skin and/or tissues under the skin (hereinafter referred as "depot sites") before being gradually taken into the systemic circulation (hereinafter referred as "depot effect"). For example, this depot effect is believed to be at least partially responsible for the delayed appearance of the fentanyl in the systemic circulation after the application of a fentanyl dermal delivery system, such as Duragesic® dermal fentanyl patch (distributed by Janssen Pharmaceutica, Inc. of Piscataway, N.J., USA), and for continued delivery of the fentanyl into the systemic circulation after the removal of the fentanyl dermal delivery system from the skin.

After placing a TADS on the skin, the analgesic concentration in the blood typically remains at or near zero for a period of time, before starting to gradually increase and reach a concentration deemed to be medicinally beneficial, called the "therapeutic level"(the time it takes to reach the therapeutic level is referred to hereinafter as the "onset time"). Ideally, the concentration of the analgesic in the bloodstream should plateau (i.e., reach a substantially steady state) at a level slightly higher than the therapeutic level and should remain there for extended period of time. For a given person and a given TADS, the "concentration of the analgesic in the bloodstream vs. time" relationship usually cannot be altered under normal application conditions.

The onset time and the delivery rate of the analgesic into the targeted area(s) of the body for a TADS are usually determined by several factors, including: the rate of release of the analgesic from the formulation, the permeability of the analgesic across the rate limiting membrane (if a rate limiting membrane is utilized), the permeability of the analgesic across the skin (especially the stratum corneum layer), analgesic storage in and release from the depot sites, the permeability of the walls of the blood vessels, and the circulation of blood and other body fluid in the tissues (including the skin) under and around the TADS. Although these primary factors affecting onset time and delivery rate are known, no existing TADS is designed to have alterable delivery rate in the course of the application of the analgesic.

While a TADS works well in many aspects, current dermal analgesic delivery technology has some serious limitations, including: 1) the onset time being undesirably long for many situations; 2) the rate that the analgesic is taken into the systemic circulation or the targeted area(s) of the body cannot be easily varied once the TADS is applied onto the skin and, when the steady state delivery rate is achieved, it cannot be easily changed; and 3) the skin permeability being so low that many analgesics are excluded from dermal delivery because the amount of analgesic delivered is not high enough to reach a therapeutic level. In addition, temperature variations in the skin and the TADS are believed contribute to the variation of dermal absorption of analgesics.

It is known that elevated temperature can increase the absorption of drugs through the skin. U.S. Pat. No. 4,898,592, issued Feb. 6, 1990 to Latzke et al., relates to a device for the application of heated transdermally absorbable active substances which includes a carrier impregnated with a transdermally absorbable active substance and a support. The support is a laminate made up of one or more polymeric layers and optionally includes a heat conductive element. This heat conductive element is used for distribution of the patient's body heat such that absorption of the active substance is enhanced. U.S. Pat. No. 4,230,105, issued Oct. 28, 1980 to Harwood, discloses a bandage with a drug and a heat-generating substance, preferably intermixed, to enhance the rate of absorption of the drug by a user's skin. Separate drug and heat-generating substance layers are also disclosed. U.S. Pat. No. 4,685,911, issued Aug. 11, 1987 to Konno et al., discloses a skin patch including a drug component, and an optional heating element for melting the drug-containing formulation if body temperature is inadequate to do so.

However, it would be advantageous to develop methods and apparatus to improve the analgesic administration of TADSs, and, more specifically, to make the use of TADSs more flexible, controllable, and titratable (varying the analgesic delivery rate, amount, or period according to the biological effect of the analgesic) to better accommodate various clinical needs.

SUMMARY OF THE INVENTION

The present invention relates to methods and apparatus for improving transdermal administration of fentanyl and sufentanil through the use of controlled heat.

Although the following discussion is focused primarily on the use of fentanyl, it is, of course, understood that the discussion is equally applicable to sufentanil, which is a structurally similar to fentanyl. It is further understood that the discussion also applies to other analgesics that are potent, so that transdermal delivery is possible. Such analgesics include: dihydroetophine, bupremorphine, hydromorphine, lerophanol, butorphanol, and oxymorphine.

In the application of transdermal analgesic deliver system (TADS), such as a Duragesic® dermal fentanyl patch (distributed by Janssen Pharmaceutica, Inc. of Piscataway, N.J., USA), the absorption of the analgesic is usually determined by a number of factors including; the diffusion coefficient of analgesic molecules in the drug formulation, the permeability coefficient of the analgesic across the rate limiting membrane (if one is used in the TADS), the concentration of dissolved analgesic in the formulation, the skin permeability to the analgesic, analgesic storage in and release from the depot sites (sites in the skin and /or sub-skin tissues in which dermally absorbed analgesic molecules are stored before being gradually released into other parts of the body), the body fluid (including blood) circulation in the skin and/or other tissue under the skin, and permeability of the walls of capillary blood vessels in the sub-skin tissues. Thus, in order to address the limitation of the current dermal analgesic delivery technologies, it is desirable to have control over and have the capability to alter these factors. It is believed that controlled heating can potentially affect each one of the above factors.

Specifically, increased temperature generally can increase diffusion coefficients of the analgesics in the formulations and their permeability across the rate limiting membrane and skin. Increased heat also increases the blood and/or other body fluid flow in the tissues under the TADS, which should carry the drug molecules into the systemic circulation at faster rates. Additionally, increased temperature also increases the permeability of the walls of the capillary blood vessels in the sub-skin tissues. Thus, the present invention uses controlled heating to affect each of the above factors for obtaining controllable dermal absorption of analgesics.

The present invention also uses controlled heating in several novel ways to make dermal analgesic delivery more flexible and more controllable in order to deal with various clinical conditions and to meet the needs of individual patients. More broadly, this invention provides novel methods and apparatus for controlled heating (hereinafter "temperature control apparatus") during the application of the TADS, such that heating can be initiated, reduced, increased, and stopped to accommodate the needs.

Another embodiment of the present invention is to determine the duration of controlled heating on TADS based on the effect of the analgesic for obtaining adequate amount of the heat-induced extra analgesic and minimizing under-treatment and side effects associated with under and over dosing.

Through the proper selection, based on the specific application and/or the individual patient's need, of the moment(s) to initiate controlled heating, heating temperature, and moment(s) to stop the controlled heating, the following control/manipulation of the absorption rates should be achieved: 1) shorten the onset time of the analgesic in the TADS without significantly changing its steady state delivery rates; 2) provide proper amount of extra analgesic during the application of a TADS when needed; and 3) increase the analgesic absorption rate throughout a significant period of duration or throughout the entire duration of the TADS application.

Shortening of onset time is important in situations where the TADS provides adequate steady state deliver rates, but the onset is too slow. Providing the proper amount of extra analgesic is important where a TADS delivers adequate "baseline" amount of the analgesic, but the patient needs extra analgesic at particular moment(s) for particular period(s) of time during the application of the TADS. Increasing the analgesic absorption rate is used for the patients who need higher analgesic delivery rates from the TADS.

The first of above approach may be achieved by applying controlled heating at the starting time of the TADS application, and design the heating to last long enough to cause the concentration of the analgesic in the systemic circulation or other targeted area of the body to rise to near the therapeutic levels, and stops (may be gradually) shortly after that. The second approach may be achieved by applying controlled heat when a need to obtain extra analgesic are rises, and terminating the controlled heating either at a predetermined moment or when the desired effect of the extra analgesic is achieved. The third approach can be achieved by applying the controlled heat at the starting time of the TADS application. In all those three approaches, temperature of the controlled heating needs to be designed to control the degree of increase in said that analgesic delivery rates.

Such embodiments are particularly useful in situations where the user of a TADS get adequate analgesic absorption most of the time, but there are periods of time in which increased analgesic absorption is desirable. For example, during the treatment of cancer patients with an analgesic, such as with Duragesic® dermal fentanyl patches, "breakthrough" pain (a suddenly increased and relatively short lasting pain, in addition to a continuous "baseline" pain) may occur. An additional analgesic dose, in the form of a tablet, an oral of nasal mucosal absorption dosage form, or an injection needs to be given to treat the breakthrough pain. With the help of controlled heat, a heating patch can be placed on top of the Duragesic® patch when an episode of breakthrough pain occurs to deliver more fentanyl into the systemic circulation. The heating duration of the heating patch is preferably designed to be long enough to deliver sufficient extra fentanyl, but not long enough to deliver the extra amount of fentanyl that may pose a risk to the patient. The patient may also remove the heating patch when the breakthrough pain begins to diminish. Thus, with the help of controlled heat, one single Duragesic® dermal fentanyl patch may take care of both baseline pain and episodes of breakthrough pain.

Due to low permeability of the skin, onset times of TADS, such a Duragesic fentanyl patch, can be undesirably long. Thus, another aspect of the present invention is to provide methods and apparatus for using controlled heat to shorten the onset times of TADSs, preferably without substantially changing the steady state drug delivery rates. A particulary useful application of this aspect of the present invention is to provide a controlled heating apparatus for use with conventional, commercially available TADSs, such as Duragesic® fentanyl patch, to shorten the onset times in clinical use, without having to re-design the TADSs or adjust their steady state drug delivery rates.

For instance, fentanyl is currently administered transdermally through a skin patch (Duragesic®). While Duragesic® delivers fentanyl at adequate rates after the lag time in many situation, it has several limitations:

1) The lag time is too long in may situation;
2) The fentanyl delivery rate into the systemic circulation is not designed to be alterable, although there are situation where increased fentanyl absorption rates are desirable. For example, it would be desirable for a cancer patient wearing a Duragesic® patch to be able tocontrol cancer pain by obtaining more fentanyl when an episode of "breakthrough" pain occurs, but with the current technology, the patient can not obtain additional fentanyl from the same Duragesic® patch;
3) Limited commercially available doses. Currently, Duragesic® only has 4 commercially available doses; 25, 50, 75 and 100 µg/hour patches. A patient can not get a delivery rate that is between these rates, or higher than 100 µg/hour.

With the technology discussed above, all these limitations may be addressed.

It is believed that an important cause for variation in analgesic absorption in TADSs is variation in temperature of the TADSs and the adjacent skin caused by variation in ambient temperature and/or physical condition of the person. This temperature variation can, of course, potentially affect all of the factors that collectively determine the ultimate analgesic deliver rates of the TADSs. Thus the present invention of providing methods and apparatus to use controlled heating is also expected to minimize the variation in the temperature of the skin and the TADSs applied on the skin. It is also contemplated that an insulating material can be incorporated with the controlled temperature apparatus to assist in not only minimizing the temperature variation, but also increasing the temperature of the TADS and the skin under it (by decreasing heat loss), each of which tend to increase dermal drug absorption.

The present invention also relates to methods and apparatus for using an insulating device, such as a cover made of insulating material (i.e. closed-cell foam tape) with adhesive edges, and a size slightly larger than the TADS to cover the TADS when the TADS and the skin of the user is exposed to extreme temperature (i.e. hot shower or hot tub bath; direct sunshine).

An important area in modern anesthesiology is patient controlled analgesia (hereinafter "PCA"), in which the patient gives himself a dose of analgesic when he feels the need. The ranges of the dose and dosing frequency are usually set by a care giver (i.e. caring physician, nurse, etc.). In many PCA situations, the patient receives a baseline rate of analgesic, and gets extra bolus analgesic when he feels that is needed. The technology in the present invention may be used for a PCA in which the patient gets the baseline dose by a regular dermal analgesic patch and the extra ("rescue") dose by heating the dermal analgesic patch. The heating temperature and duration needs to be designed to deliver a proper amount of extra dose.

One of the more important aspects of the present invention is the apparatus for generating and providing controlled heating. These controlled heat generating apparatus generally comprise a heat generating portion and means to pass the heat generated by the heat generating portion to the TADSs, the skin, and/or the sub-skin depot and storage sites. These controlled heat generating apparatus generally further include a mechanism (such as tape, adhesive, and the like) for affixing the apparatus onto the TADSs and/or the skin. Preferably, the affixation mechanism securely holds the controlled heat generating apparatus in place while in use, but it also allows relatively easy removal after use. Additionally, these controlled heat generating apparatus may further include a mechanism for termination the generation of heat. For applications with TADSs, the shape and size of the bottom of the controlled heat generating apparatus are generally specially made to accommodate the TADSs with which they are to be employed.

One embodiment of a controlled heat generating apparatus is a shallow chamber including non-air permeable side wall(s), a bottom wall, and a non-air permeable top wall which has area(s) with limited and desired air permeability (e.g., holes covered with a microporous membrane). A heat generating medium is disposed within the shallow chamber. The heat generating medium preferably comprises a mixture of iron powder, activated carbon, salt, water, and, optionally, sawdust. The controlled heat generating apparatus is preferably stored in an air-tight container from which it is removed prior to use. After removal from the air-tight container, oxygen in the atmosphere ("ambient oxygen") flows into heat generating medium through the areas on the non-air permeable top with desired air-permeability to initiate a heat generating oxidation reaction (i.e., an exothermic reaction). The desired heating temperature and duration can be obtained by selecting the air exposure of the top (e.g., selecting the right size and number of holes on the cover and/or selecting the microporous membrane covering the holes for a specific air permeability), and/or by selecting the right quantities and/or ratios of components of the heat generating medium.

This embodiment of the controlled heat generating apparatus preferably includes a mechanism for affixing the controlled heat generating apparatus onto the skin or a TADS that is applied to the skin. For applications where the removal or termination of the heating might be necessary, the heat generating apparatus may also have a mechanism for allowing easy removal from the TADS and/or the skin or for termination of the heating. One mechanism for allowing easy removal of the shallow chamber from a TADS without removing the latter from the skin comprises a layer of adhesive on the side walls of the heat generating apparatus with an non-adhesive area or less adhesive area (less adhesive than the adhesive affixing the TADS to the skin) at the bottom of the shallow chamber, with the non- or less adhesive area having a shape similar to that of the TADS. When such a heat generating apparatus is applied onto the TADS which is on the skin, the adhesive at the bottom of the side walls of the heat generating apparatus adheres to the skin, and non- or less adhesive part is on top of, but not adhered or not strongly adhered to the TADS. This allows for removal of the heat generating apparatus without disturbing the TADS.

Although one application of such a heat generating apparatus is to be used in connection with a TADS, it is understood that the heat generating apparatus can also be applied directly to the skin to increase the release of drugs from depot sites.

The heat generating mechanism of the present invention for the controlled heat generating apparatus is not limited to the preferred exothermic reaction mixture of iron powder, activated carbon, salt, water, and, optionally, sawdust, but may include a heating unit whose heat is generated by electricity. The electric heating unit, preferably, includes a two dimensional surface to pass the heat to the TADS and/or the skin. The electric heating unit may also include a temperature feedback system and temperature sensor that can be placed on the TADS of the skin. The temperature sensor monitors the temperature at the TADS or skin and transmits an electric signal based on the sensed temperature to a controller which regulates the electric current or voltage to the electric heating unit to keep the temperature at the TADS or skin at desired levels. Preferably, a double sided adhesive tape can be used to affix the electric heating unit onto the skin.

The heat generating mechanism may also comprise an infrared generating unit and mechanism to direct the infrared radiation onto the TADS or the skin. It may also have a temperature feedback system and temperature sensor that can by placed on the TADS or the skin to control the intensity of the infrared emission to maintain the temperature at the TADS or skin at desired levels.

The heat generating mechanism may further comprise a microwave generation unit and a mechanism to direct the microwave radiation onto the TADS or the skin. Again, the heat generating mechanism may have a temperature feedback system and a temperature sensor to regulate the intensity of the microwave emission to maintain the temperature at the TADS or skin at desired levels.

The heat generating mechanism may yet further comprise a container containing supercooled liquid which generates heat from crystallization ("exothermic"). The crystallization is initiated withing the container, such as by bending a metal piece in the supercooled liquid, and the container in placed on a TADS or on the skin. The heat which is released from the crystallization process is passed to the TADS and/or the skin. However, heat generated by crystallization usually does not maintain a constant level over extended time. Thus, such a heat generating mechanism is not ideal for application where elevated temperature is a narrow range over and extended time is necessary, but is useful where only a short heating duration is needed, such as with a TADS or an injected controlled/extended release analgesic formulation which is capable of releasing adequate amounts of extra drug by such heating when needed.

BRIEF DESCRIPTION OF THE DRAWINGS

While the specification concludes with claims particularly pointing out and distinctly claiming that which is regarded as the present invention, the objects and advantages of this invention may be more readily ascertained from the following description of the invention, when read in conjunction with the accompanying drawings in which:

DETAILED DESCRIPTION OF THE ILLUSTRATED EMBODIMENT

FIGS. 1–24 illustrate various views of temperature control or other apparatuses and transdermal analgesic delivery systems. It should be understood that the figures presented in conjunction with this description are not meant to be illustrative of actual views of any particular apparatus, but are merely idealized representations which are employed to more clearly and fully depict the present invention than would otherwise be possible. Elements common between the figures retain the same numeric designations.

Figure 1:
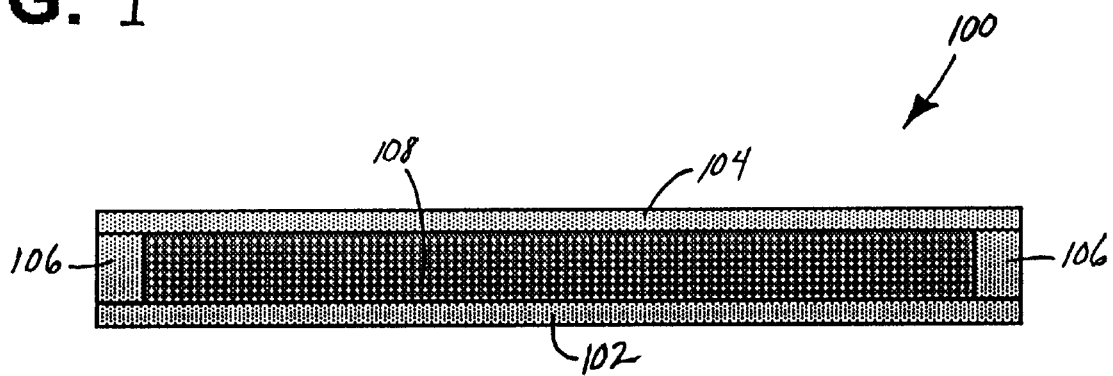
FIG. 1 is a side cross-sectional view of an embodiment of a temperature control apparatus according to the present invention.

FIG. 1 illustrates a temperature control apparatus 100 of the present invention comprising a chamber defined by a bottom wall 102, a top wall 104, and side walls 106 wherein a temperature regulating mechanism 108 is disposed within the chamber. The temperature regulating mechanism 108 can include a heat generating oxidation reaction mechanism, electric heating unit, exothermic crystallization mechanism, endothermic crystallization mechanism, heating/cooling mechanism, cooling mechanism, or the like.

Figure 2:
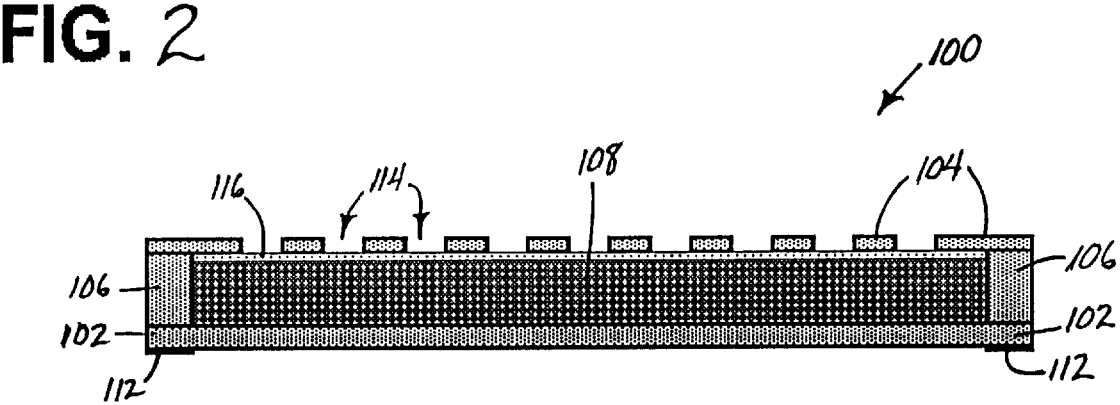
FIG. 2 is a side cross-sectional view of another embodiment of a temperature control apparatus according to the present invention.

FIG. 2 illustrates a temperature control apparatus 100 comprising a temperature regulating mechanism 108 surrounded by a bottom wall 102, a top wall 104, and side walls 106. The bottom wall 102 is preferably a plastic material and the side walls 106 are preferably made of a flexible non-air permeable material, such as non-air permeable closed-cell foam material. A portion or all of the bottom wall 102 of the temperature control apparatus 100 includes an adhesive material 112 for attachment to a TADS or to the skin of a patient. The temperature regulating mechanism 108 preferably comprises a composition of activated carbon, iron powder, sodium chloride and water in a proper ratio. Optionally, saw dust may be added to the composition to facilitate the airflow within the composition and/or provide "body" to the composition. The top wall 104 is preferably also a flexible non-air permeable material having holes 114 therethrough. An air permeable membrane 116 is, preferably, disposed between the top wall 104 and the temperature regulating mechanism 108 to regulate the amount of air reaching the temperature regulating mechanism 108 through the holes 114. The air permeable membrane 116 is preferably a porous film (such as No. 9711 microporous polyethylene film—CoTran™, 3M Corporation, Minneapolis, Minn., USA).

Figure 3:
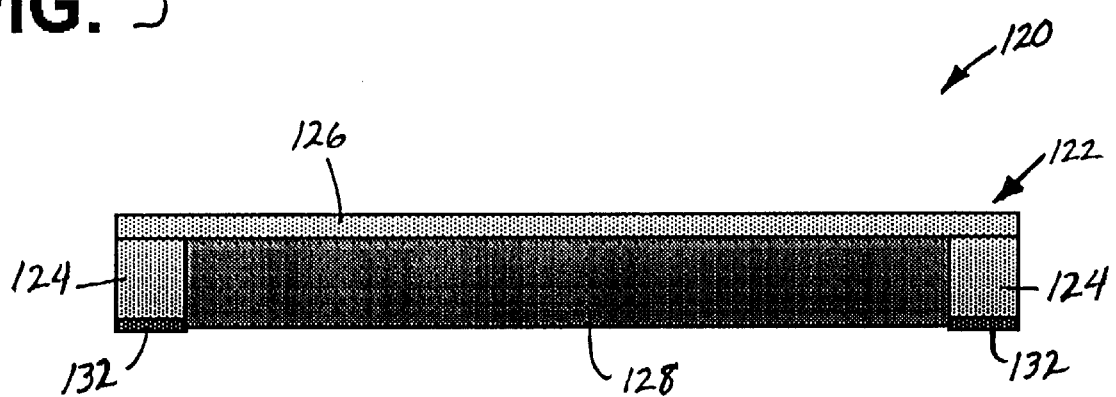
FIG. 3 is a side cross-sectional view of an embodiment of a transdermal analgesic delivery system according to the present invention.

FIG. 3 illustrates a transdermal analgesic delivery system 120 (hereinafter "TADS 120") comprising a housing 122 made of a flexible material(s). The housing 122 preferably comprises side walls 124 and a top wall 126 with an analgesic formulation 128 disposed within the housing 122. Preferably, the bottom of the TADS side walls 124 include an adhesive 132 to affix the TADS 120 to the skin of a patient.

Figure 4:
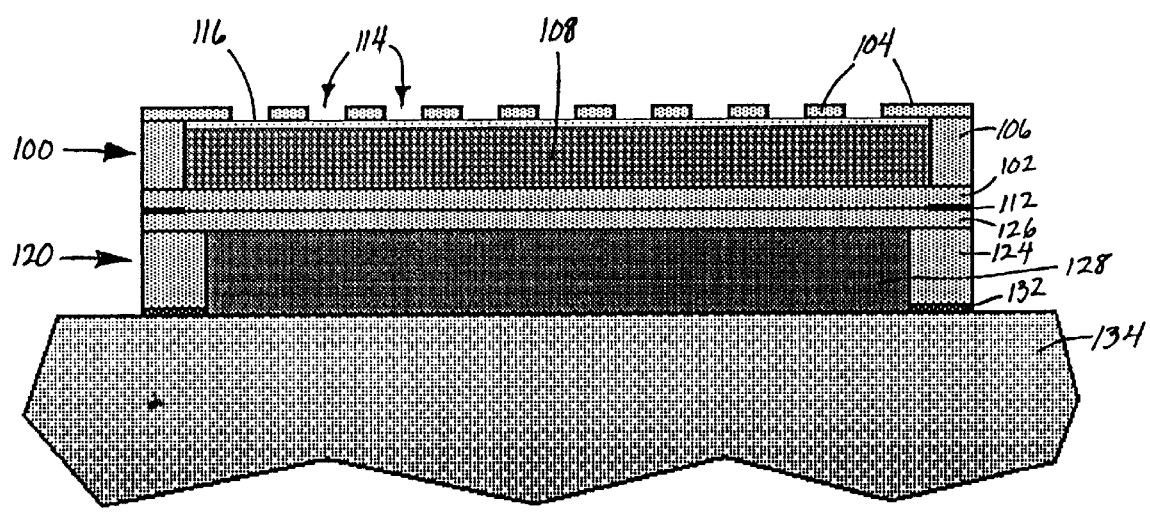
FIG. 4 is a side cross-sectional view of the temperature control apparatus of FIG. 2 in conjunction with the transdermal analgesic delivery system of FIG. 3 according to the present invention.

FIG. 4 illustrates the temperature control apparatus 100 of FIG. 2 attached to the TADS 120 of FIG. 3. The TADS 120 attached to a portion of the skin 134 of a patient. The area of the temperature regulating mechanism 108 is preferably slightly larger than that of the analgesic formulation 128. The temperature control apparatus 100 and the TADS 120 are preferably stored in separated compartments of an air tight container (or in separate air tight containers).

EXAMPLE 1

One example of using the embodiment of the present invention illustrated in FIGS. 2–4 for administering analgesic material for relief of pain consists of a patient or care giver placing the TADS 120 on the skin 134 of the patient, which preferably adheres to the skin 134 with TADS adhesive 132. The patient or care giver then attaches the temperature control apparatus 100 on top of the TADS 120, which adheres to the TADS 120 with temperature control apparatus adhesive 112. Oxygen in ambient air flows into the temperature regulating mechanism 108 through holes 114 and air permeable membrane 116. Of course, it is understood that the rate at which oxygen contacts the temperature regulating mechanism 108 is determined by the size and number of the holes 114 on the top wall 104, as well as the air permeability of the air permeable membrane 116. A heat generating (exothermic) chemical reaction occurs in the temperature regulating mechanism 108. Heat from this reaction passes through the temperature control apparatus bottom wall 102, through the TADS top wall 126, through the analgesic formulation 128, and increases the temperature of the patient's skin 134 under the TADS 120.

In actual experimentation, the temperature control apparatus 100 comprised the side walls 106 defined by a 1/8 inch thick rectangular foam tape (2 layers of No.1779 1/16" white foam tape, 3M Corporation, Minneapolis, Minn., USA) with an outer dimension of about 2.25 inches by 4 inches with an opening therein having an inner dimension of about 1.75 inches by 3.5 inches, the bottom wall 102 comprising rectangular medical tape (No. 1525L plastic medical tape, 3M Corporation, Minneapolis, Minn., USA) of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA) with forty-five holes 114 (diameters approximately 0.9 mm, in a 5 by 9 pattern with about 7.5 mm to 8.0 mm center spacing) therethrough. The side walls 106, the bottom wall 102, and the top wall 104 defined a chamber. The holes 114 of the top wall 104 were covered by an air permeable membrane 116 comprising a porous membrane (No. 9711 microporous polyethylene film—CoTran™, 3M Corporation, Minneapolis, Minn., USA) disposed between the top wall 104 and the temperature regulating mechanism 108. The side walls 106, the bottom wall 102, and the top wall 104 all had 1/8" rounded corners. The temperature regulating mechanism 108 disposed in the chamber comprised a mixture of activated carbon (HDC grade—Novit Americas, Inc., USA), iron powder (grade R1430—ISP Technologies, USA), saw dust (Wood Flour, Pine—Pioneer Sawdust, USA), sodium chloride and water in the weight ratio of approximately 5:16:3:2:6 weighing approximately 16.5 grams. The temperature control apparatus 100 was sealed in an air-tight container immediately after fabrication.

Figure 5:
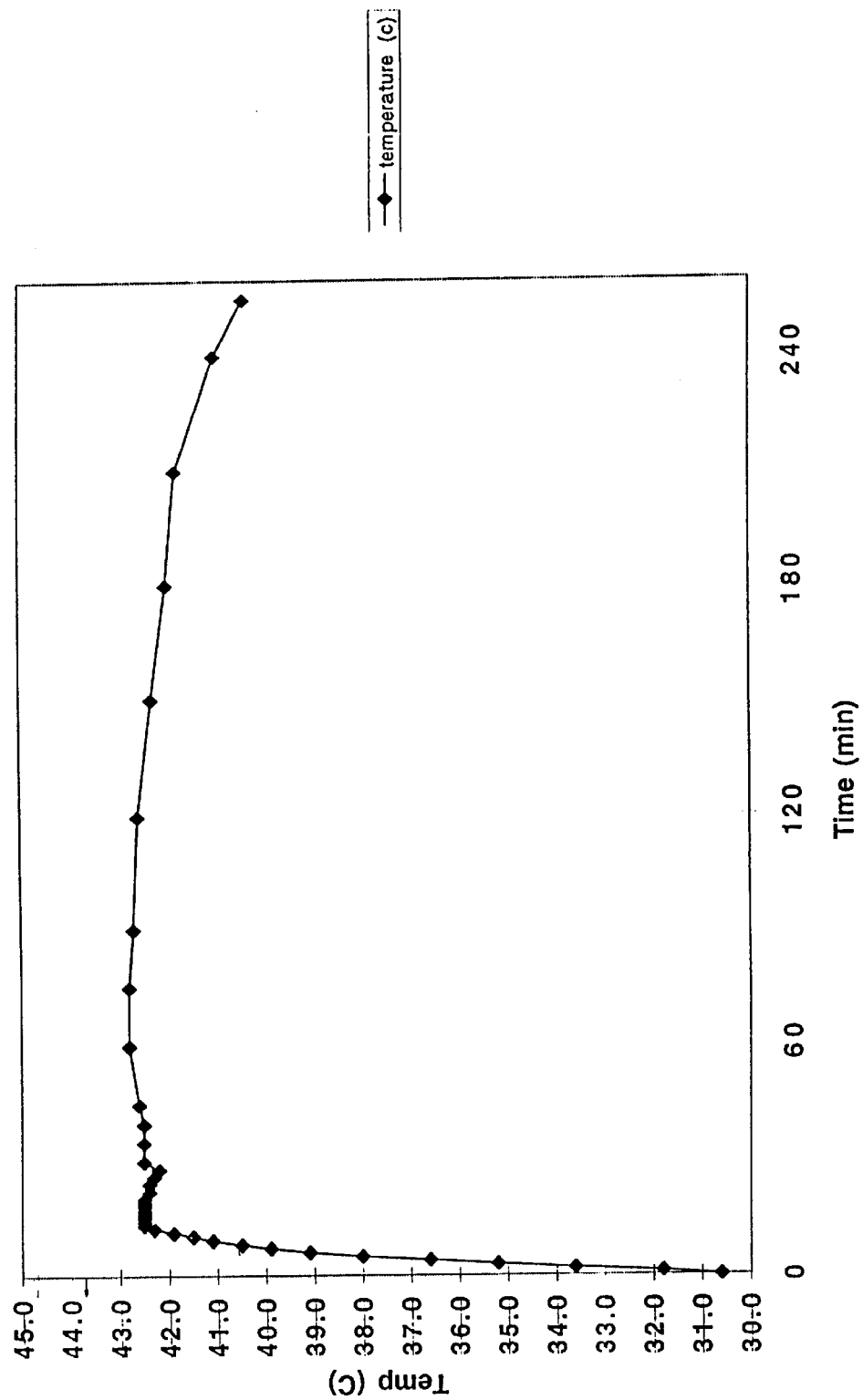
FIG. 5 is a graph of time versus temperature for a temperature control apparatus according to the present invention.

The temperature control apparatus 100 was tested on a volunteer with a temperature probe placed between the temperature control apparatus 100 and the volunteer's skin to measure the temperature. The results of this temperature experiment is illustrated in FIG. 5 and Table A, which shows that the temperature control apparatus 100 is capable of keeping the skin temperature to a narrow, elevated range of about 41° C. to 43° C. for extended period of time (at least about 240 minutes).

TABLE A

| Time (minutes) | Temperature (° C.) |
| --- | --- |
| 0 | 30.6 |
| 1 | 31.8 |
| 2 | 33.6 |
| 3 | 35.2 |
| 4 | 36.6 |
| 5 | 38.0 |
| 6 | 39.1 |
| 7 | 39.9 |
| 8 | 40.5 |
| 9 | 41.1 |
| 10 | 41.5 |
| 11 | 41.9 |
| 12 | 42.3 |
| 13 | 42.5 |
| 14 | 42.5 |
| 15 | 42.5 |
| 16 | 42.5 |
| 17 | 42.5 |
| 18 | 42.5 |
| 19 | 42.5 |
| 20 | 42.5 |
| 22 | 42.4 |
| 24 | 42.4 |
| 26 | 42.3 |
| 28 | 42.2 |
| 30 | 42.5 |
| 35 | 42.5 |
| 40 | 42.6 |
| 45 | 42.6 |
| 60 | 42.5 |
| 75 | 42.8 |
| 90 | 42.7 |
| 120 | 42.6 |
| 150 | 42.3 |
| 180 | 42.0 |
| 210 | 41.8 |
| 240 | 41.0 |
| 255 | 40.4 |

Nine human volunteers receive a dose of fentanyl in a TADS 120. The TADS 120 comprised a commercially available dermal fentanyl patch, Duragesic-50® (designed to deliver an average of 50 micrograms of fentanyl per hour). The experiment was conducted to determine fentanyl concentrations within the volunteers' blood (over a 12 hour period) without heating the TADS 120 and with heating the TADS 120 (with the temperature control apparatus 100 described above). The experiments were conducted with at least a two week time period between the heated and unheated sessions. In the unheated session, the TADS 120 was applied onto the volunteer's chest skin and removed after about 240 minutes. In the heated session, the TADS 120 was applied onto the subject's chest skin and immediately cover by the temperature control apparatus 100. Both the TADS 120 and the temperature control apparatus 100 were removed after about 240 minutes. In both sessions, blood samples were taken at various intervals for 12 hours and the fentanyl concentrations in serum samples were determined by radioimmunoassay.

Figure 6:
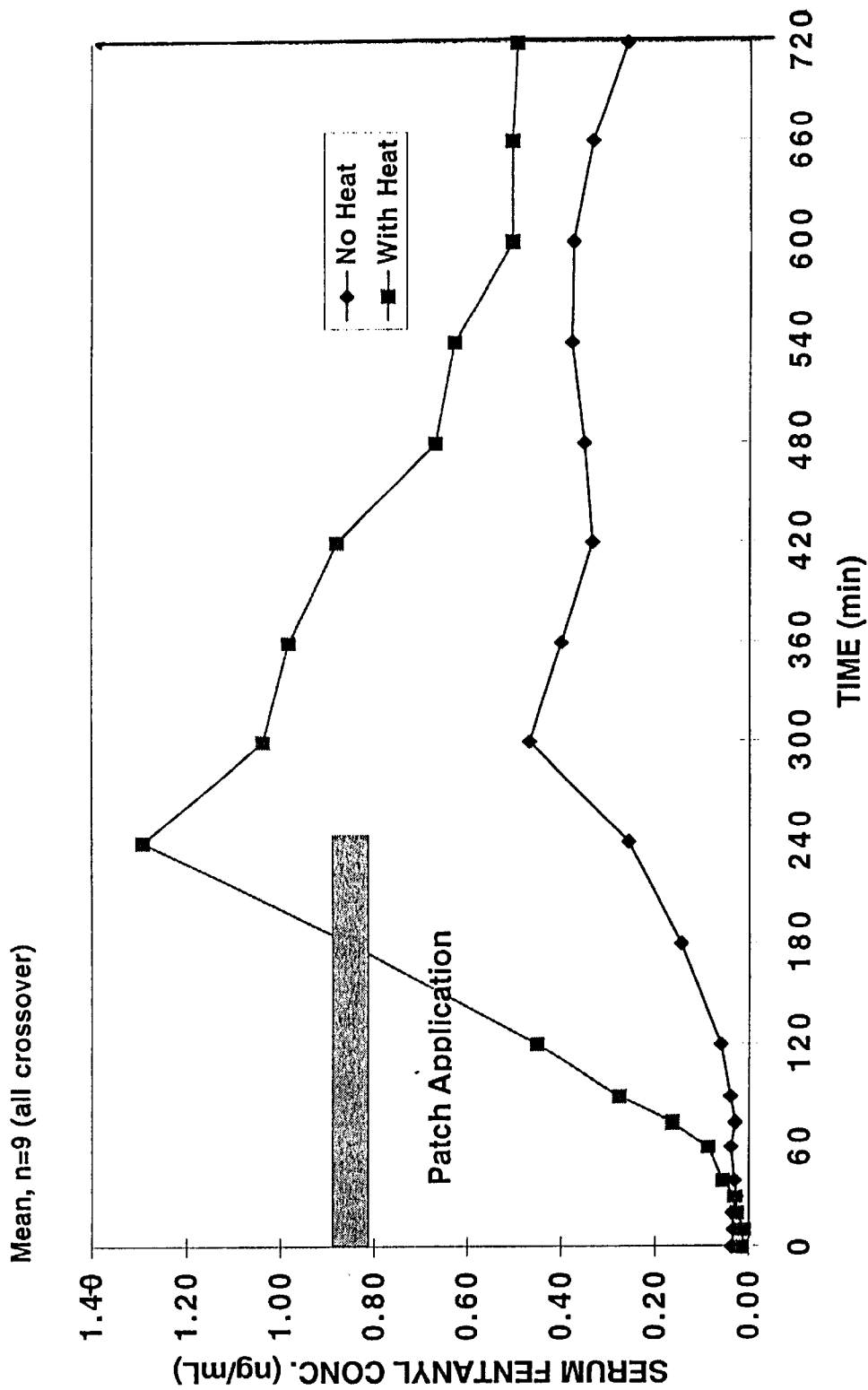
FIG. 6 is a graph of the mean fentanyl concentration of nine volunteers verse time for a four hour contact of a fentanyl containing TADS with heating and without heating according to the present invention.

FIG. 6 and Table B illustrates the mean serum fentanyl concentrations produced by the heated and unheated Duragesic-50® patches, respectively, over a 720 minute duration (The lowest standard used in the assay was 0.11 ng/ml. Concentrations lower than 0.11 ng/ml were obtained using an extrapolation method.). With heating by the temperature control apparatus 100, it was found that fentanyl began to enter the systemic circulation earlier, and at faster rates. At 240 minutes, the end of the heating and fentanyl patch application, the average serum concentrations of fentanyl in the volunteers with the heating of the Duragesic-50® patch was about 5 times that of the unheated Duragesic-50®. These surprising results demonstrates that controlled heat can significantly increase the speed of dermal fentanyl absorption and shorten the onset time.

TABLE B

| Time (minutes) | Serum Fentanyl Conc. Without Heat (ng/ml) | Serum Fentanyl Conc. With Heat (ng/ml) |
| --- | --- | --- |
| 0 | 0.04 | 0.01 |
| 10 | 0.03 | 0.01 |
| 20 | 0.03 | 0.02 |
| 30 | 0.03 | 0.03 |
| 40 | 0.03 | 0.06 |
| 60 | 0.04 | 0.09 |
| 75 | 0.03 | 0.16 |
| 90 | 0.04 | 0.28 |
| 120 | 0.06 | 0.45 |
| 180 | 0.14 | 0.85 |
| 240 | 0.26 | 1.29 |
| 300 | 0.47 | 1.04 |
| 360 | 0.40 | 0.98 |
| 420 | 0.33 | 0.88 |
| 480 | 0.35 | 0.67 |
| 540 | 0.38 | 0.63 |
| 600 | 0.37 | 0.51 |
| 660 | 0.33 | 0.50 |
| 720 | 0.26 | 0.49 |

Thus, it is believed that the increased temperature increases the skin permeability (compared with a TADS without such a heating mechanism), which results in the fentanyl entering the patient's systemic circulation faster. This should result in serum fentanyl concentrations reaching steady state quicker. The heating is also believed to increase the body fluid circulation and blood vessel wall permeability in the sub-skin tissues, and cause fentanyl to spend less time in the sub-skin depot site. As a result, the patient receives the analgesic compound more quickly and receives improved pain relief.

Figure 7:
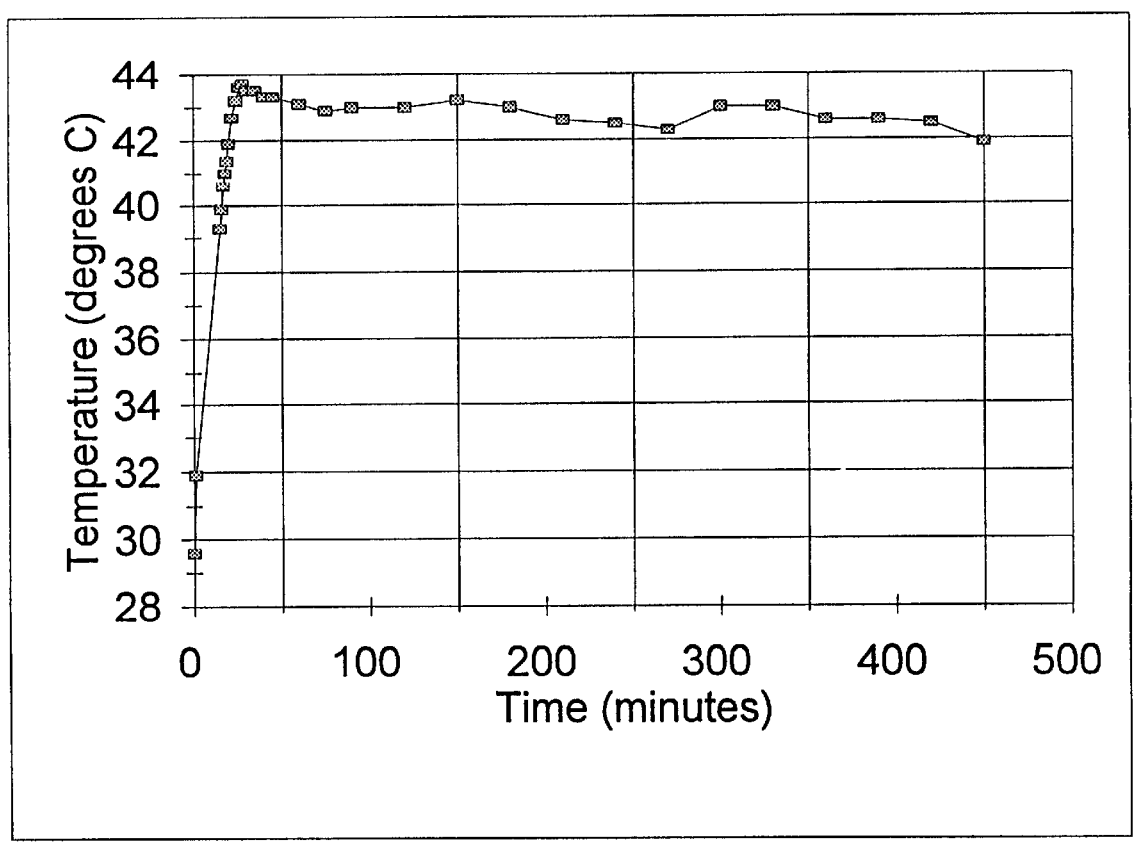
FIG. 7 is a graph of time versus temperature for a temperature control apparatus according to the present invention.

In yet another experiment, the temperature control apparatus 100 comprised the side walls 106 defined by a 3/16 inch thick rectangular foam tape (3 layers of No. 1779 1/16" white foam tape, 3M Corporation, Minneapolis, Minn., USA) with an outer dimension of about 2.25 inches by 4 inches with an opening therein having an inner dimension of about 1.75 inches by 3.5 inches, the bottom wall 102 comprising rectangular medical tape (No. 1525L plastic medical tape, 3M Corporation, Minneapolis, Minn., USA) of a dimension of about 2.25 inches by 4 inches with a non-adhesive side attached to the bottom of the side walls 106, and a top wall 104 comprising a rectangular 1/32 inch thick foam tape (No. 9773 1/32" tan foam tape, 3M Corporation, Minneapolis, Minn., USA) with seventy-eight holes 114 therethrough (diameters approximately 1/32 inch, in a 6 by 13 pattern with about a 6 mm center spacing). The side walls 106, the bottom wall 102, and the top wall 104 define a chamber. The holes 114 of the top wall 104 are covered by an air permeable membrane 116 comprising a porous membrane (No. 9711 CoTran™ membrane, 3M Corporation, Minneapolis, Minn., USA) disposed between the top wall 104 and the temperature regulating mechanism 108. The side walls 106, the bottom wall 102, and the top wall 104 all had 1/8" rounded corners. The temperature regulating mechanism 108 disposed in the chamber comprised a mixture of activated carbon, iron powder, saw dust, sodium chloride and water in the weight ratio of approximately 5:16:3:2:6 weighing approximately 25 grams. This temperature control apparatus 100 was tested on a volunteer's stomach with a temperature probe placed between the temperature control apparatus 100 and the volunteer's skin to measure the temperature. The results of this temperature experiment is illustrated in FIG. 7 and Table C, which shows that the temperature control apparatus 100 is capable of keeping the skin temperature to a narrow, elevated range at between about 41 and 44° C. for extended period of time (at least about 450 minutes).

TABLE C

| Time (minutes) | Temperature (° C.) |
| --- | --- |
| 0 | 29.6 |
| 1 | 31.9 |
| 15 | 39.3 |
| 16 | 39.9 |
| 17 | 40.6 |
| 18 | 41.0 |
| 19 | 41.4 |
| 20 | 41.9 |
| 22 | 42.7 |
| 24 | 43.2 |
| 26 | 43.6 |
| 28 | 43.7 |
| 30 | 43.5 |
| 35 | 43.5 |
| 40 | 43.3 |
| 45 | 43.3 |
| 60 | 43.1 |
| 75 | 42.9 |
| 90 | 43.0 |
| 120 | 43.0 |
| 150 | 43.2 |
| 180 | 43.0 |
| 210 | 42.6 |
| 240 | 42.5 |
| 270 | 42.3 |
| 300 | 43.0 |
| 330 | 43.0 |
| 360 | 42.6 |
| 390 | 42.6 |
| 420 | 42.5 |
| 450 | 41.9 |

Figure 8:
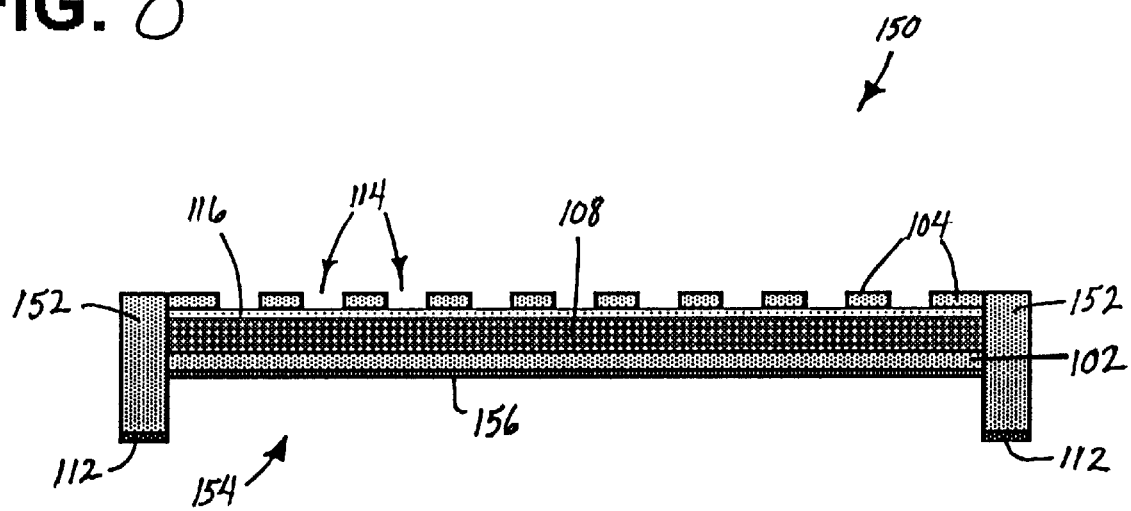
FIG. 8 is a side cross-sectional view of another embodiment of a temperature control apparatus according to the present invention.

FIG. 8 illustrates another embodiment of a temperature control apparatus 150 comprising a temperature regulating mechanism 108 surrounded by a bottom wall 102, a top wall 104, and side walls 152. The side walls 152 extend a distance below the bottom wall 102 to define a cavity 154. The bottom wall 102 is preferably made of plastic tape material and the side walls 152 are preferably made of a flexible non-air permeable material, such as non-air permeable closed-cell foam material. A portion of the bottom of the temperature control apparatus 150 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. Again, the temperature regulating mechanism 108 preferably comprises a composition of activated carbon, iron powder, sodium chloride, water, and, optionally, saw dust. The top wall 104 is preferably also a flexible non-air permeable material having holes 114 therethrough. An air permeable membrane 116 is disposed between the top wall 104 and the temperature regulating mechanism 108 to regulate the amount of air reaching the temperature regulating mechanism 108 through the holes 114.

Figure 9:
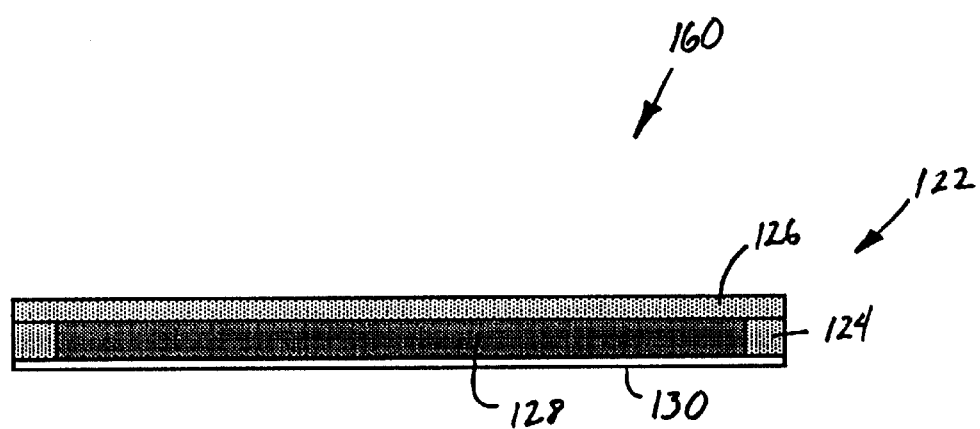
FIG. 9 is a side cross-sectional view of another embodiment of a transdermal analgesic delivery system according to the present invention.

FIG. 9 illustrates a TADS 160 comprising a housing made 122 of flexible materials. The housing 122 preferably comprises side walls 124 and a top wall 126 with an analgesic formulation 128 disposed within the housing 122, and may include a membrane 130 which may be a rate-limiting membrane.

Figure 10:
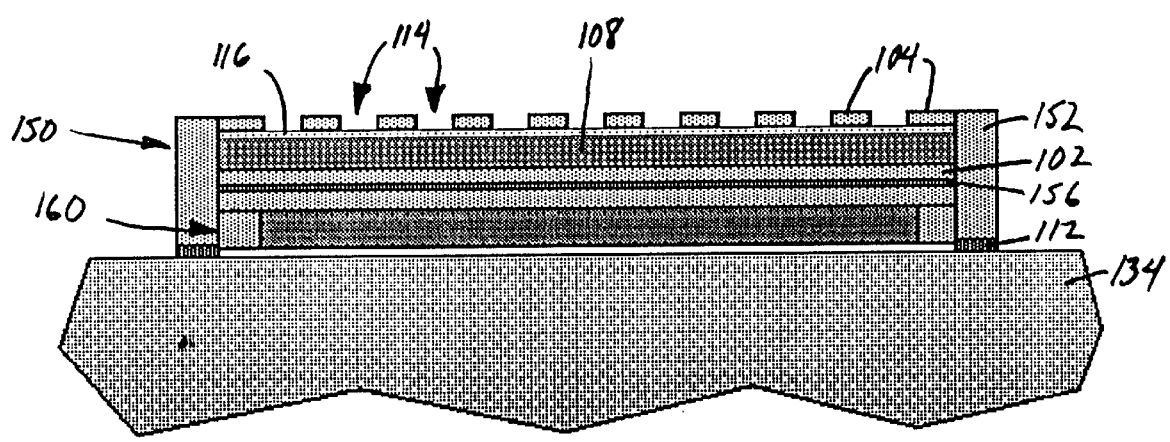
FIG. 10 is a side cross-sectional view of the temperature control apparatus of FIG. 8 in conjunction with the transdermal analgesic delivery system of FIG. 9 according to the present invention.

FIG. 10 illustrates the temperature control apparatus 150 of FIG. 8 attached to the TADS 160 of FIG. 9. The TADS 160 is placed on (or attached with an adhesive, not shown) a portion of the skin 134 of a patient and the temperature control apparatus 150 is placed over the TADS 160, such that the TADS 160 resides within the cavity 154 (see FIG. 8). The adhesive material 112 attaches to the skin 134 and holds the temperature control apparatus 150 in place. If the TADS 160 is not attached to the skin 134, the temperature control apparatus 150 holds the TADS 160 in place. Preferably, the TADS 160 is attached to the skin 134 with an adhesive material (not shown) with the temperature control apparatus 150 placed over the TADS 160. The temperature control apparatus 150 is attached to the skin 134 with the adhesive material 112 and the second adhesive material 156 (less adhesive than any attachment adhesive (not shown) between the TADS 160 and the skin 134 and less adhesive than the adhesive material 112 between the temperature control apparatus 150 and the skin 134) attaches the temperature control apparatus 150 to the TADS 160. Such an arrangement results in secure adhesion of the temperature control apparatus 150 and the TADS 160 to the skin 134, yet allows for the removal of the temperature control apparatus 150 without removing the TADS 160.

Figure 11:
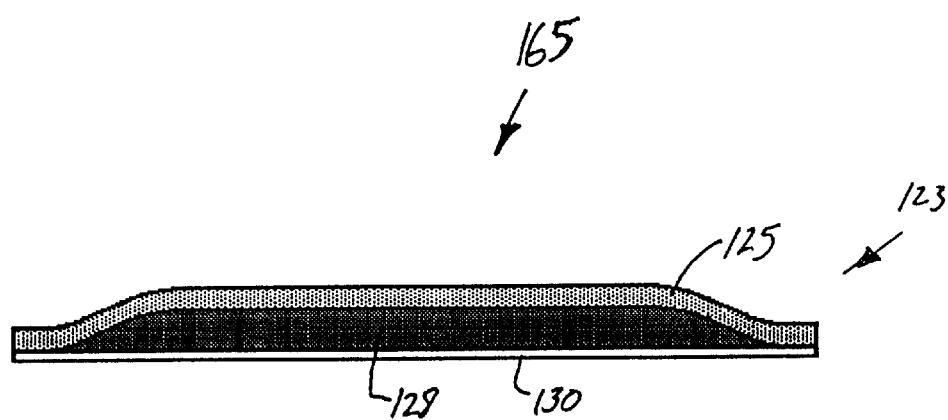
FIG. 11 is a side cross-sectional view of still another embodiment of a transdermal analgesic delivery system according to the present invention.
Figure 12:
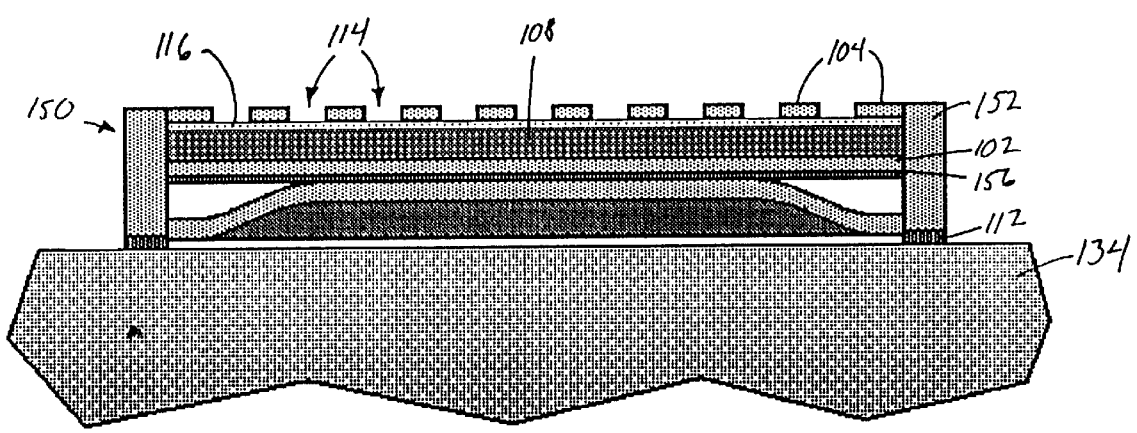
FIG. 12 is a side cross-sectional view of the temperature control apparatus of FIG. 8 in conjunction with the transdermal analgesic delivery system of FIG. 11 according to the present invention.

FIG. 11 illustrates an alternate TADS 165 comprising a housing 123 made of flexible material(s). The housing 123 preferably comprises top wall 125 and a membrane 103, which may be a rate-limiting membrane, with an analgesic formulation 128 disposed within the housing 123. FIG. 12 illustrates the temperature control apparatus 150 of FIG. 8 attached to the TADS 165 of FIG. 11, similar that described for FIG. 10.

EXAMPLE 2

An example of using the embodiment of the present invention illustrated in FIGS. 8–12 for administering analgesic material to treat breakthrough pain consists of a patient or care giver placing the TADS 160, 165 on the skin 134 of the patient with the temperature control apparatus 150 placed thereover. By way of example, when the TADS 160, 165 is a commercially available fentanyl patch, Duragesic-50®, it takes several hours after the application of the TADS 160, 165 to obtain a sufficient steady state level of fentanyl in the patient's bloodstream to control baseline pain. However, such as with the treatment of cancer patients, a patient will from time to time suffer breakthrough pain, which is a suddenly increased but usually not long lasting pain. When a patient feels that a breakthrough pain episode is imminent, the patient places the temperature control apparatus 150 over the TADS 160, 165. The heat from the temperature control apparatus 150 increases the temperature of the fentanyl patch, the skin, and tissues under the skin. As a result, more fentanyl is absorbed across the skin. Furthermore, fentanyl already in the skin and sub-skin depot sites (i.e., fentanyl molecules that have already permeated across the skin but were stored in the skin and sub-skin tissues) starts to be released into the systemic circulation at faster rates because of increased blood/body fluid flow in the tissues under the fentanyl patch and increment blood vessel wall permeability caused by heat from the temperature control apparatus 150. The overall result is that fentanyl concentration in the patient's bloodstream is significantly increased shortly after the heating patch is applied (compared with no temperature control apparatus 150 being used), and the increased fentanyl in the bloodstream alleviates the breakthrough pain in a timely manner. It is believed that for lipophilic compounds, such as fentanyl, that usually have significant dermal depot effect (storage in depot sites in the skin and sub-skin tissues and gradual release from the depot sites), the increased analgesic release from the depot sites due to the heating may make a more rapid and a more significant contribution to increasing bloodstream drug concentrations than the contribution from increased skin permeability caused by the heat. The patient may leave the heating patch on for a pre-determined length of time, based on his previous experience of breakthrough pain, before he stops the heating by removing the patch or placing an air impermeable tape to cover all the holes on the top wall 104. The patient may also stop the heating when he feels the current episode of breakthrough pain is over or beginning to end.

Preferably, the heating patch is designed to have a pre-determined heating duration that is sufficient to treat most patients' breakthrough pain, but not long enough to cause serious side effects associated with fentanyl overdose. However, if a particular patient has a higher tolerance to fentanyl, the patient can use two or more of the heating patches consecutively so that the patient gets just enough extra fentanyl to treat the breakthrough pain.

EXAMPLE 3

Yet another example of using the embodiment of the present invention illustrated in FIGS. 8–12 comprises using the temperature control apparatus 150 for administering analgesic material to treat pain when the diffusion coefficient of the active ingredients in the formulation 128 and/or permeability coefficient across a rate limiting membrane 130 is so low that it dominantly determines the overall absorption rate of analgesic material from the TADS 160, 165 into a patient's body. By way of example with the use of a TADS 160, 165, the patient or care giver places the TADS 160, 165 on the skin 134 of the patient. If after a time of wearing the TADS 160, 165, it is determined that for this particular patient and his conditions a higher concentration of fentanyl in the bloodstream is required to properly treat his pain, the temperature control apparatus 150 is placed on top of the TADS 160, 165 to heat the TADS 160, 165.

The increased temperature increases diffusion coefficient of the active ingredient in the formulation in the TADS 160, 165 and increases the permeability coefficient across the rate limit membrane 130 in the TADS 160, 165, and, thus, the overall rates at which the active ingredient enters the patient's body. This, in turn, increases the concentration of active ingredient in the bloodstream. As a result, the patient gets the increased and proper effect.

EXAMPLE 4

Still another example of using the embodiment of the present invention illustrated in FIGS. 8–12 comprises using the temperature control apparatus 150 for decreasing onset time of an analgesic material from the TADS 160, 165. By way of example with the use of a commercially available fentanyl patch, such as Duragesic-50®, as the TADS 160, 165, the patient or care giver places the TADS 160, 165 on the skin 134 of the patient and places the temperature control apparatus 150 over the TADS 160. Preferably, the temperature control apparatus 150 includes a sufficient amount of activated carbon, iron powder, sodium chloride, and water in the temperature regulating mechanism 108 to sustain an exothermic reaction for at least 4 hours.

The heat from the temperature control apparatus 150 increases the temperature at a contact surface of the skin 134 and the TADS 160, 165 to temperatures up to about 60° C., preferably a narrow temperature range between about 36° C. and 46° C., most preferably between 37° C. and 44° C., and maintains this temperature for a period of time (i.e., approximately 4 hours). During this time, the heat increases the speed of fentanyl release from the TADS 160, 165, the permeation rate across the skin 134, the permeation of blood vessel walls, and the speed of blood circulation which carriers the fentanyl into the systemic circulation faster. The exothermic reaction is designed to cease (gradually) after the therapeutic fentanyl in serum is achieved or about to be achieved. As a result, the fentanyl absorption and concentration in the bloodstream begins to decrease from the elevated levels caused by the heat from the TADS 160, 165 returns to normal (unheated) levels. The patient continues to wear the system for a total of between about 48 and 72 hours. Compared with a TADS 160, 165 without the use of the temperature control apparatus 150, the fentanyl begins to appear in the bloodstream significantly earlier to yield a shortened onset time and the fentanyl concentrations in the bloodstream in the early hours of application are significantly higher than that produced by an unheated TADS 160, 165. The therapeutic serum fentanyl concentration varies from person to person. For example some people respond to levels above 0.2 ng/mL. Referring to FIG. 6, this 0.2 ng/mL concentration is achieved in about one-third the amount of time for a heated system than for a non-heated system (i.e., about 70 minutes as compared with about 210 minutes).

After a period of time when the exothermic reaction of temperature control apparatus 150 slowly stops generating heat, the fentanyl concentration in the bloodstream starts to gradually approach the normal steady state fentanyl concentrations in the bloodstream which would ultimately be seen with an unheated TADS 160, 165, given a sufficient amount of time. As a result, the temperature control apparatus 150 significantly shortens the onset time of Duragesic-50® without significantly altering its steady state delivery rates. Thus, the important advantage provided by this approach is that the onset time of a TADS 160, 165 already in clinical use can be shortened without significantly altering its steady state delivery rates which are not only adequate, but also familiar to the caregivers and the patients.

EXAMPLE 5

A further example of using the embodiment of the present invention illustrated in FIGS. 8–12 comprises using the temperature control apparatus 150 for a sustained high absorption rate of an analgesic material from the TADS 160, 165. Cancer patient's tend to develop a tolerance for fentanyl (and other analgesic materials) after extended use. For example, if a patient becomes tolerant to a Duragesic-100® (100 micrograms/hour deliver rate) dermal patch, a care giver may apply both a Duragesic-100® and a Duragesic-50® (50 micrograms/hour delivery rate) to treat the patient's cancer pain. However, instead of using two Duragesic® patches, a care giver can use a Duragesic-75® (75 micrograms/hour delivery rate) patch in conjunction with the temperature control apparatus 150, preferably designed to last between about 12 and 24 hours, to increase the fentanyl absorption. The care giver replaces the heating patch, after the designed heating during is over, with another heating patch to maintain a desired temperature, and continues to do so until the fentanyl in the Duragesic-75® patch can no longer supply a therapeutic amount of fentanyl. It is, of course, understood that the temperature control apparatus 150 may be designed to last as long as the expected usage time of the Duragesic-75® dermal patch.

Heating patches with different heating temperatures may be used to achieve different increased levels of fentanyl deliver rates.

Figure 13:
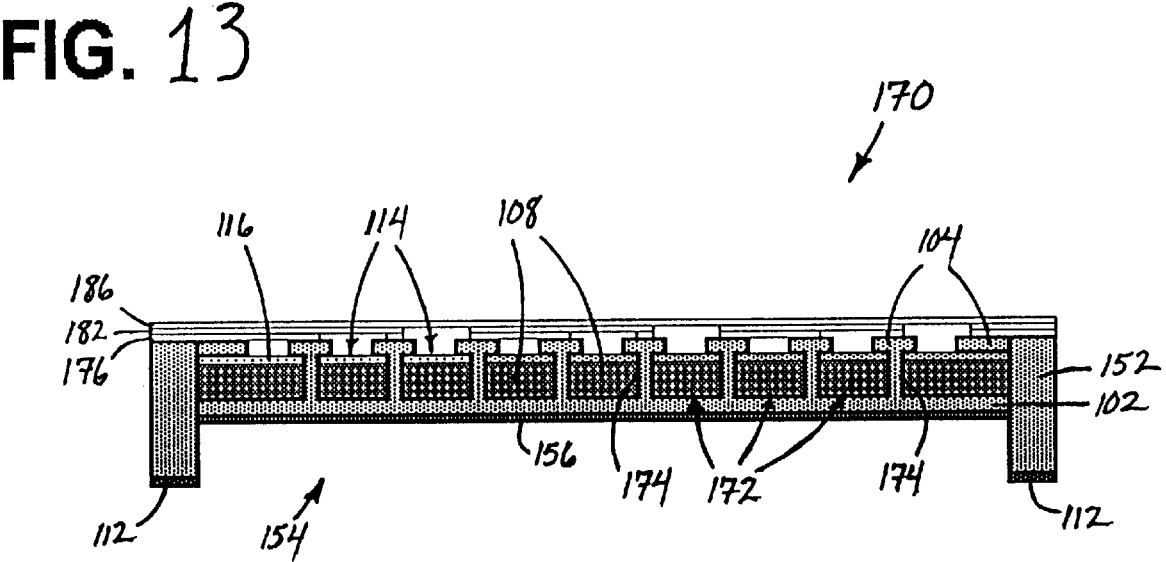
FIG. 13 is a side cross-sectional view of yet another embodiment of a temperature control apparatus having three cover layers over an oxygen activated temperature regulating mechanism chambers according to the present invention.
Figure 14:
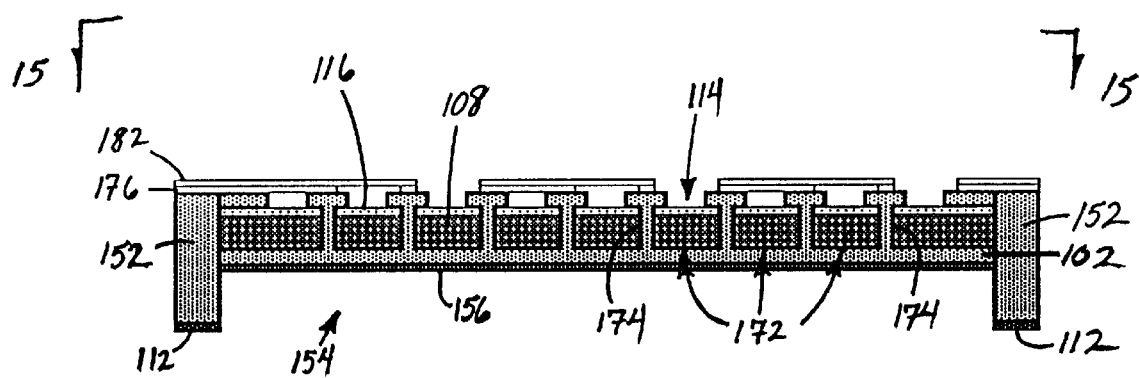
FIG. 14 is a side cross-sectional view of the temperature control apparatus of FIG. 13 having a first cover layer removed according to the present invention.
Figure 15:
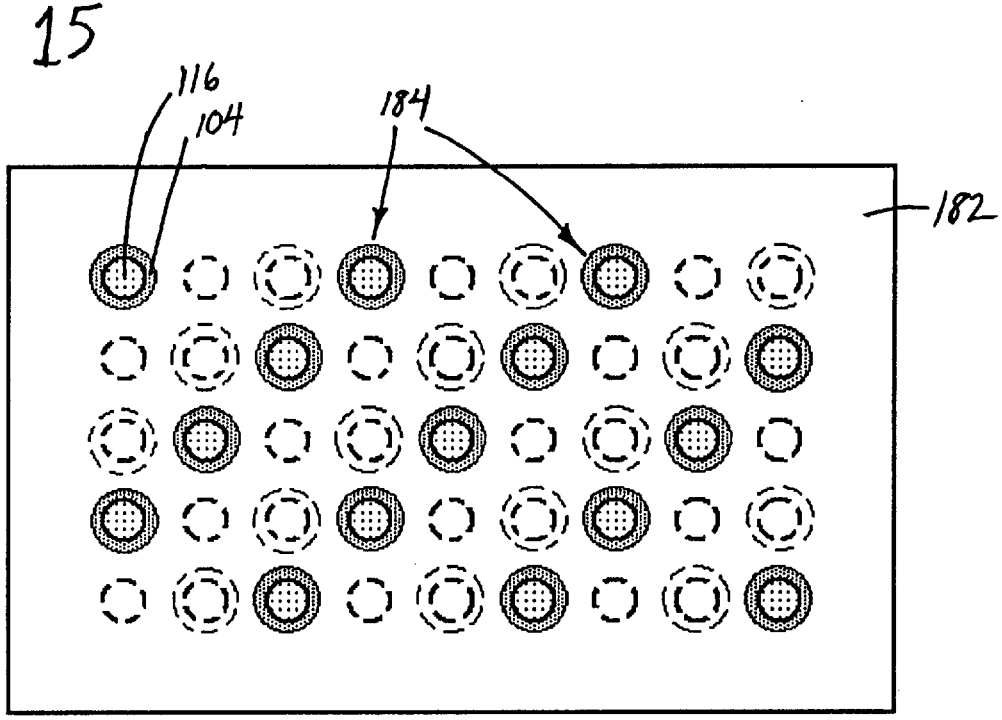
FIG. 15 is a top plan view of the temperature control apparatus of FIG. 14 along line 15—15 according to the present invention.
Figure 16:
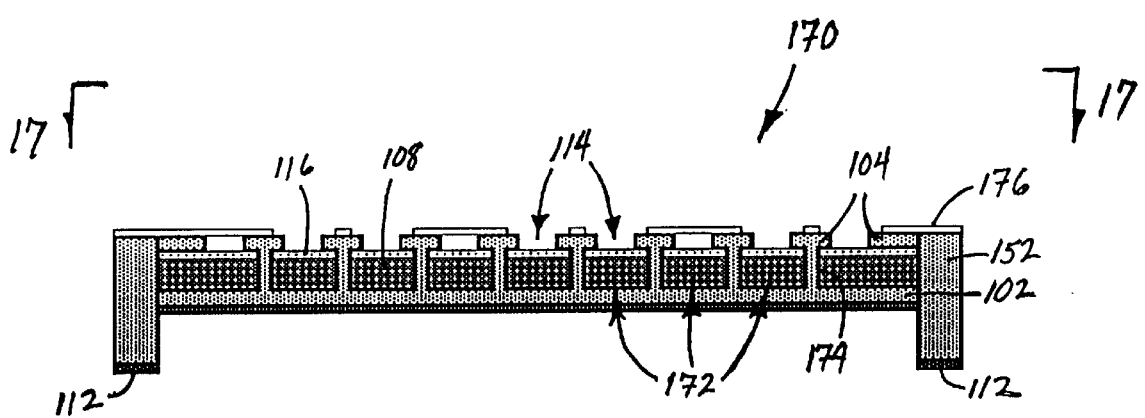
FIG. 16 is a side cross-sectional view of the temperature control apparatus of FIG. 14 having a second cover layer removed according to the present invention.
Figure 17:
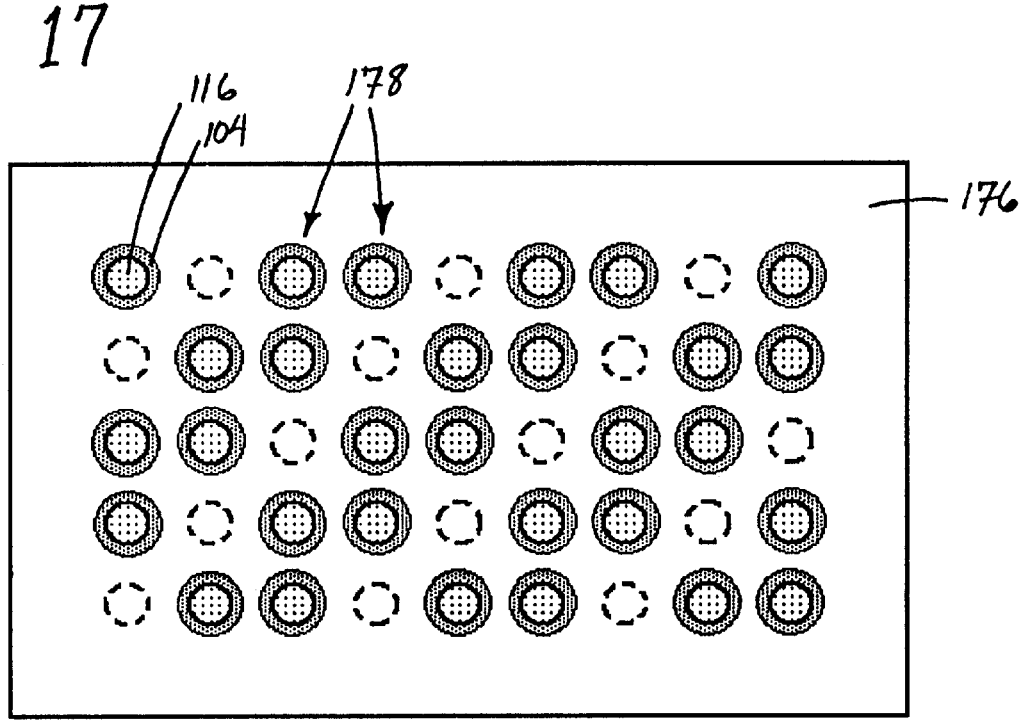
FIG. 17 is a top plan view of the temperature control apparatus of FIG. 16 along line 17—17 according to the present invention.
Figure 18:
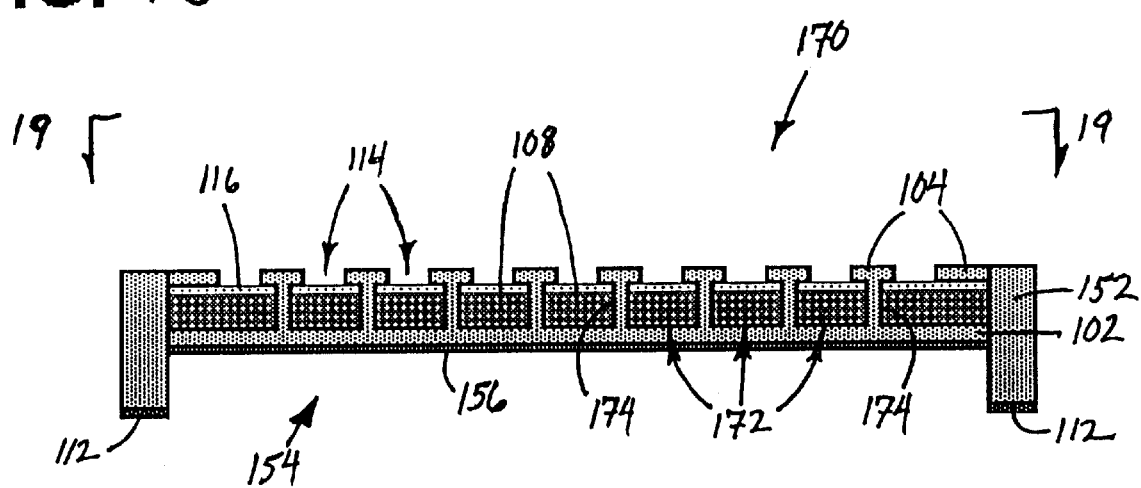
FIG. 18 is a side cross-sectional view of the temperature control apparatus of FIG. 16 having a third cover layer removed according to the present invention.
Figure 19:
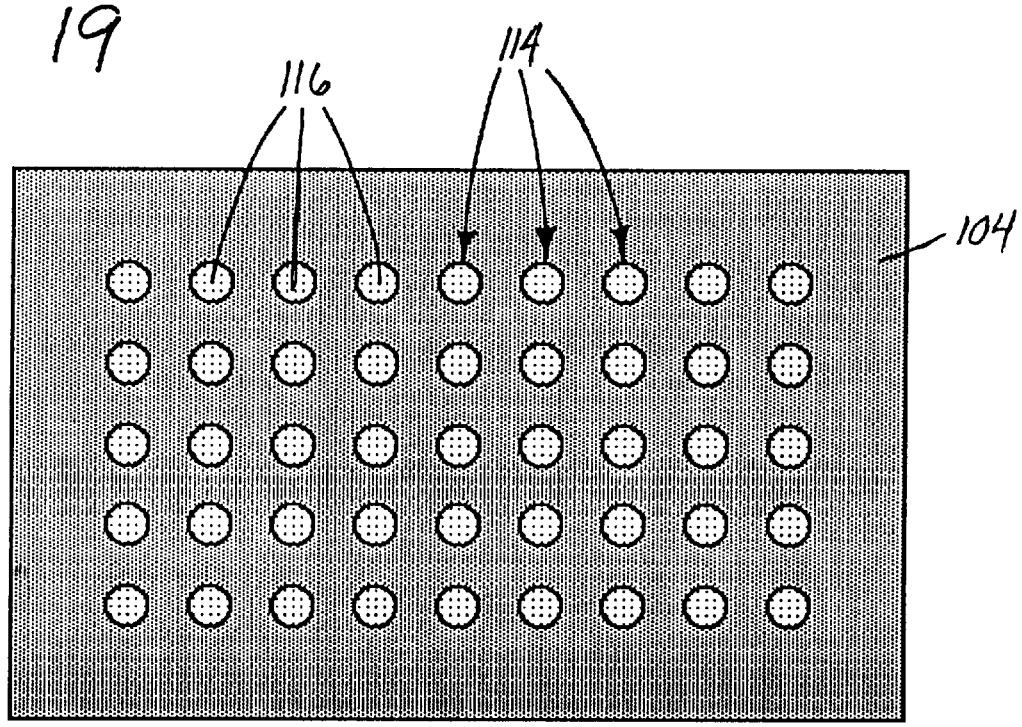
FIG. 19 is a top plan view of the temperature control apparatus of FIG. 18 along line 19—19 according to the present invention.

FIGS. 13–19 illustrates another embodiment of a temperature control apparatus 170. FIG. 13 illustrates the temperature control apparatus 170 which is similar to the embodiment of FIG. 8, but comprises a temperature regulating mechanism 108 which is made up of a plurality of chambers 172 separated by non-air permeable walls 174. The temperature regulating mechanism 108 is substantially surrounded by a bottom wall 102, a top wall 104, and side walls 152. Again, the temperature regulating mechanism 108 preferably comprises a composition of activated carbon, iron powder, sodium chloride, water, and, optionally, saw dust, which is disposed in each of the chambers 172. The top wall 104 is preferably also a flexible non-air permeable material having a plurality of holes 114 therethrough, preferably, a row of holes 114 for each chamber 172. An air permeable membrane 116 is disposed between the top wall 104 and the temperature regulating mechanism 108 to regulate the amount of air reaching the temperature regulating mechanism 108 through the holes 114. The top wall 104 can have at least one cover covering the plurality of holes 114 for the regulation of the air into the chambers 172. As illustrated in FIG. 13, three covers are layered on the top wall 104. A first cover layer 176 is affixed to the top wall 104 and has openings 178 (see FIG. 17) to expose 2 out of 3 holes 114. A second cover layer 182 is affixed to the first cover layer 176 and has opening 184 (see FIG. 15) to expose 1 out of 3 holes 114. A top cover 186, which has no openings, is affixed to the second cover layer 182. Thus, a patient has a various opinions on what percentage of chambers 172 to expose to ambient air. If the heat generated from one third of the chambers is required, the top cover 186 is removed, as shown in FIGS. 14 and 15. If the heat generated from two thirds of the chambers is required or if another additional heat is needed after the depletion of the first one-third of the temperature regulating mechanism 108, the top cover 186 and the second cover layer are removed, as shown in FIGS. 16 and 17. If the heat generated from all of the chambers is required or if another additional heat is needed after the depletion of the first and second one-third of the temperature regulating mechanism 108, the top cover 186, the second cover layer 182, and the first cover layer 176 are removed, as shown in FIGS. 18 and 19. It is, of course, understood that more or less cover layers can be used with any number of holes to results in any desired amounts of the temperature regulating mechanism 108 being activated.

Thus, by way of example a patient can have a number of choices in using the temperature control apparatus 170, such for the suppression of breakthrough pain. When the breakthrough pain occurs, the patent places the temperature control apparatus 170 over an analgesic material TADS and can do any of the following:

1) Activate a particular number or percent of chambers 172 by removing the requisite covers depending on how much additional analgesic material is required to treat the breakthrough pain. The covers can be preferably replaced to stop the exothermic reaction when no more additional analgesic material is required.

2) Activate a particular number or percent of chambers 172, exhaust the heat generating capacity of those chambers 172, and then activate other (non-activated) chambers 172. This extends the heating duration of the temperature control apparatus 170. The duration of the total heating time is determined by the typical duration of the particular patient's breakthrough pain.

3) Activate enough chambers 172 to treat one episode of breakthrough pain, and leave the heating patch in place. When the next episode of breakthrough pain occurs, activate unused chambers 172.

Figure 20:
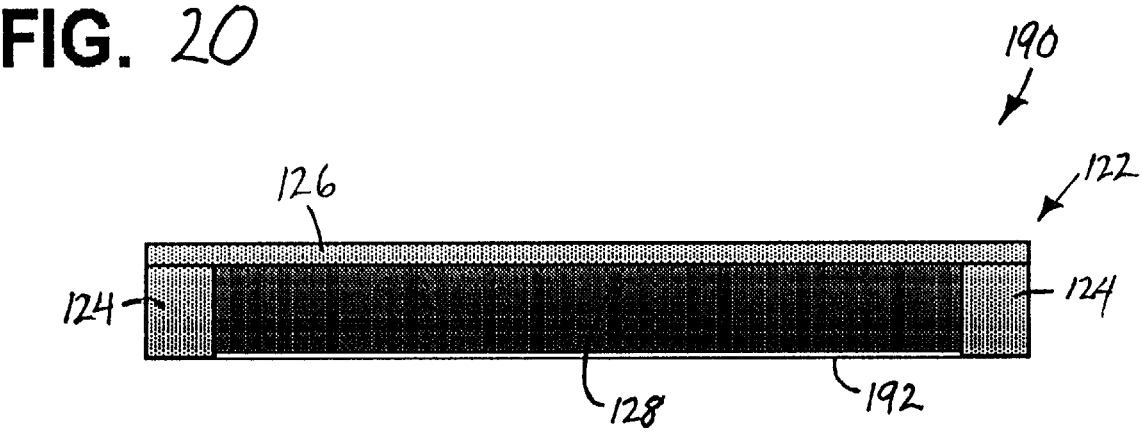
FIG. 20 is a side cross-sectional view of another embodiment of a transdermal analgesic delivery system having a rate limiting membrane according to the present invention.

FIG. 20 illustrates a transdermal analgesic delivery system 190 (hereinafter "TADS 190") having a rate limiting membrane 192. The structure of TADS 190 is similar to that of FIG. 3. However, the TADS 190 includes a rate limiting membrane 192 which resides between the analgesic formulation 128 and the skin 134 of a patient.

Generally, the permeability of the analgesic in the analgesic formulation 128 through the rate limiting member 192 is significantly lower than the permeability of the analgesic in the analgesic formulation 128 into the skin of an average patient. Rate limiting membranes 192 are used to minimize the variation in overall permeation, and to regulate the amount of analgesic delivered to the patient so that overdosing does not occur. Another aspect of the present invention is the use of a temperature sensitive rate limiting membrane, such that the analgesic permeation rate through the rate limiting membrane increases significantly with increasing temperature. With such a TADS 190, the above discussed temperature control mechanisms 100 (FIGS. 1 & 2), 150 (FIG. 8), and 170 (FIG. 13) can be used to increase the analgesic delivery rate across the rate limiting membrane 192 to treat breakthrough pain, reduce onset time, increase steady state delivery rate, or other advantages discussed above.

Figure 21:
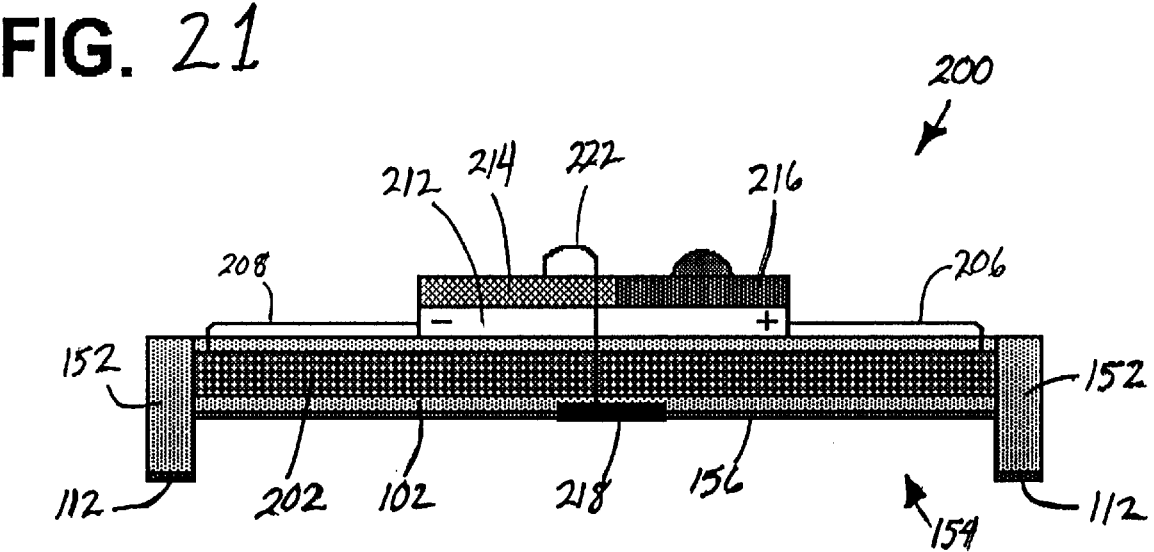
FIG. 21 is a side cross-sectional view of an electric temperature control mechanism according to the present invention.

The possible temperature control mechanisms are not limited to the exothermic reaction mixture of iron powder, activated carbon, salt, water, and sawdust, as discussed above. FIG. 21 illustrates an electric temperature control mechanism 200 comprising an electric heating element 202 surrounded by a bottom wall 102, a top wall 104, and side walls 152 (similar to FIG. 8). The side walls 152, preferably, extend a distance below the bottom wall 102 to define a cavity 154. It is, of course, understood that the electric heating element 202 does not have to have the side walls 152 forming a cavity 154.

The bottom wall 102 and the side walls 152 are preferably made of a flexible non-air permeable material, such as non-air permeable closed-cell foam material. A portion of the bottom of the temperature control apparatus 200 includes an adhesive material 112 on the bottom of the side walls 152 and, preferably, includes a second adhesive material 156 in the bottom of the bottom wall 102, wherein the second adhesive material 156 is preferably less adhesive than the adhesive material 112. The electric heating element 202 preferably comprises a flexible resistor plate that can generate heat when supplied with an electric current through traces 206, 208. The electric current is preferably supplied from a battery 212 attached to a control mechanism 214, and an electronic switch 216. The battery 212, the control mechanism 214, and the electronic switch 216 are preferably attached to the top surface of the top wall 104. The electric heating element 202 is activated by triggering the electronic switch 216 which begins the flow of electric current from the battery 212 to the electric heating element 202. A temperature sensor 218, such as a thermistor, is preferably attached to the bottom of the bottom wall 102 and sends a signal (corresponding to the temperature at the bottom of the bottom wall 102) through electric trace 222 to the control mechanism 214. The control mechanism 214 regulates the flow of current to the electric heating element 202, so that the electric heating element 202 quickly brings the temperature at a contact surface between the bottom wall 102 and a top of a TADS (not shown) to a pre-determined level and maintains the temperature at that pre-determined level. The following features may be incorporated into the control mechanism 214: 1) a mechanism that allows a physician or care giver set the length of each heating period for each patient, which allows the physician to limit the heating, and hence the extra analgesic that the patient can get based on the conditions of the patient; 2) a mechanism that allows the physician or care giver to set the minimum time between the heating periods, and hence how often the patient can get the extra analgesic through increase heat; 3) a mechanism that allows the physician or care giver to set a pre-determined temperature; and/or 4) a mechanism that allows the physician or care giver to control the heating temperature profile, such as gradually increasing heating temperature or decreasing temperature over a pre-determined period of time. These features can potentially give simple TADSs a variety of control options for the physician and/or the patient on the qunantity and timing of the delivery of extra analgesic.

EXAMPLE 6

An example of using the embodiment of the present invention, such as illustrated in FIG. 21, includes using the temperature control mechanism 200 for a sustained high absorption rate of an analgesic material from the DDDS 160, 165. Cancer patient's tend to develop a tolerance for fentanyl (and other analgesic materials) after extended use. For example, if a cancer patient becomes tolerant to a Duragesic-100® (100 micrograms/hour deliver rate) dermal patch, a care giver may apply an electric heating device, such as temperature control mechanism 200, on a Duragesic-100® patch and sets the temperature to heat the skin surface to 38° C. to obtain a higher rate of fentanyl delivery from the Duragesic-100® patch for treating the patient's cancer pain. However, if, after a duration of treatment, the cancer patient becomes tolerant the fentanyl delivery rate at 38° C., the care giver can adjust the temperature control mechanism 200 on the of Duragesic-100® patch to heat the skin surface to 40° C. to obtain an even higher rate of fentanyl delivery from the Duragesic-100® patch for treating the patient's cancer pain.

Figure 22:
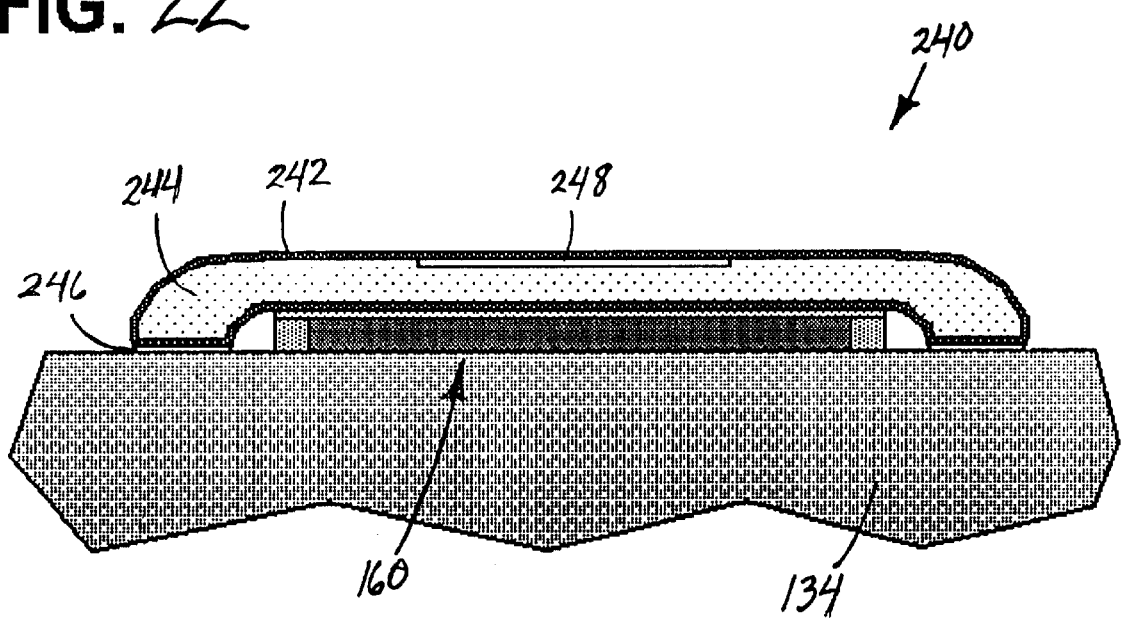
FIG. 22 is a side cross-sectional view of a temperature control apparatus comprising a flexible bag filled with a supercooled liquid according to the present invention.
Figure 23:
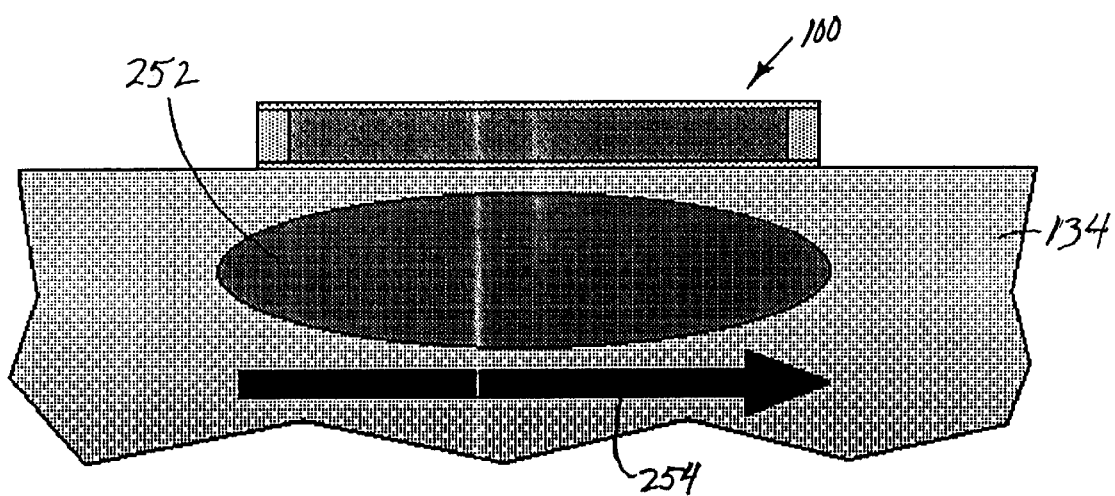
FIG. 23 is a side cross-sectional view of a temperature control apparatus applied directly to a patient's skin according to the present invention.

FIG. 22 illustrates another embodiment of a temperature control apparatus 240 comprising a substantially flat, flexible bag 242 filled with a supercooled liquid 244, such as a concentrated solution of sodium acetate. A bottom portion of the bag 242, preferably, includes an adhesive material 246. The bag 242 is preferably slightly larger than the TADS 160 such that the adhesive material 246 may contact and adhere to the skin 134. The bag 242 further includes a triggering mechanism 248, such as a metal strip. For example, when a patient wearing a TADS containing an appropriate analgesic material feels the imminent onset of breakthrough pain, the bag 242 is placed over the TADS 160. The triggering mechanism 248 is activated (such as by bending a metal strip) which triggers crystallization in the supercooled liquid. The heat generated by the crystallization (phase transition) increases the speed of transport of analgesic material into the body and the speeds the release of analgesic material from the depot sites in the skin and the sub-skin tissues. As a result the patient gets a rapid delivery of extra analgesic material to treat breakthrough pain. Usually, the heat generated by a phase transition can not be sustained over extended time, but may be enough to release adequate amount of analgesic material from the depot sites in the tissues under the skin to treat the breakthrough pain. The advantage of the temperature control apparatus 240 is that it is reusable. After use, the temperature control apparatus 240 can be placed in hot water and then cooled to room temperature to transfer the solidified contents in the bag back to a supercooled liquid 244.

EXAMPLE 7

One example of enhanced depot site absorption using the embodiment of the present invention illustrated in FIGS. 1 and 2 for administering analgesic material for pain relief consists of a patient or care giver placing the TADS, such as a fentanyl-containing TADS, on the skin of the patient at a first location. After sufficient depletion of the analgesic in the TADS, the TADS is removed and a second TADS is placed on the skin of the patient at a second location to continue analgesic delivery. If an episode of breakthrough pain occurs, the temperature control apparatus 100 can be applied directly to the patient's skin 134 at the first location (the TADS is no longer present), as shown in FIG. 22. The heat from the temperature control device 100 increases the speed of analgesic release from the depot site 252 in the first skin site and the tissues thereunder to give an increased analgesic absorption into the systemic circulation 254 to treat the breakthrough pain.

EXAMPLE 8

Figure 24:
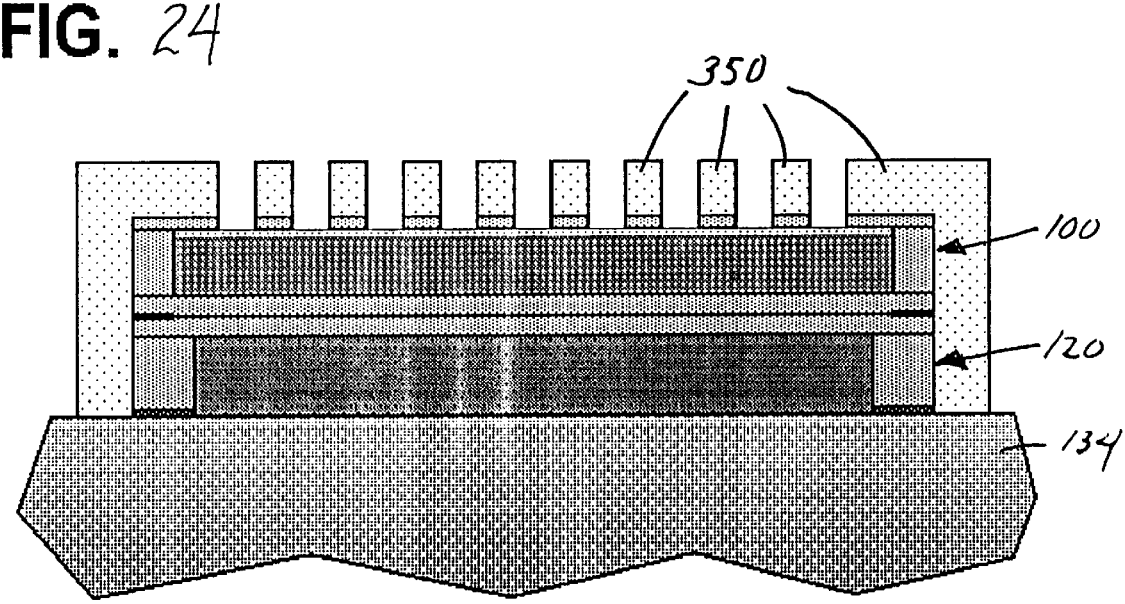
FIG. 24 is a side cross-sectional view an insulative material over a TADS for minimizing temperature variation and/or increasing the temperature of the TADS and the skin thereunder according to the present invention.

As shown in FIG. 24, an insulating material can be incorporated with the controlled temperature apparatus to assist in not only minimizing the temperature variation, but also increasing the temperature of the TADS and the skin under it (by decreasing heat loss), each of which tend to increase dermal analgesic absorption.

FIG. 24 illustrates a configuration similar to that illustrated in FIG. 4 wherein the temperature control apparatus 100 of FIG. 2 is attached to the TADS 120 of FIG. 3. The TADS 120 attached to a portion of the skin 134 of a patient. An insulating sleeve 350 abuts the skin 134 and encases a substantial portion of the temperature control apparatus 100 and the TADS 120.

It is, of course, understood that the heating devices discussed above could be replaced by an infrared heating device with a feedback mechanism. All of the controls and variations in controls discussed above would apply to such an infrared heating device. The advantage of infrared radiation over simple heat is that the former, with proper wavelengths, penetrates deeper into a patient's skin.

It is further understood that although the above examples were focused primarily on the use of fentanyl, the discussion is equally applicable to sufentanil, which is a derivative of fentanyl.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A method of controlling the rate of analgesic delivery to a systemic circulation of a human body comprising:
   applying a transdermal analgesic delivery system to the skin of said human body for delivery of an analgesic to said systemic circulation of said human body;
   applying a temperature modification apparatus capable of generating controlled heat proximate said transdermal analgesic delivery system by exposing an oxygen activated exothermic medium within the apparatus to oxygen and varying the amount of oxygen to which the exothermic medium is exposed to vary a rate of reaction of the exothermic medium; and heating said skin of said human body proximate said transdermal analgesic delivery system with said temperature modification apparatus to achieve an increased rate of delivery of analgesic to said systemic circulation of said human body.

2. The method of claim 1, wherein said applying said temperature modification apparatus capable of generating heat proximate said transdermal analgesic delivery system comprises applying said temperature modification apparatus to said transdermal analgesic delivery system.

3. The method of claim 1, wherein said heating said transdermal analgesic delivery system includes heating said skin of said human body proximate said transdermal analgesic delivery system up to a temperature of about 60° C.

4. The method of claim 1, wherein said heating said skin of said human body effectuates an increase in said rate of analgesic delivery to said systemic circulation of said human body through increasing skin permeability by said heating.

5. The method of claim 1, wherein said heating said skin of said human body effectuates an increase in said rate of analgesic delivery to said systemic circulation of said human body through increasing the permeability of blood vessel walls in sub-skin tissues by said heating.

6. The method of claim 1, wherein said heating said skin of said human body effectuates an increase in said rate of analgesic delivery to said systemic circulation of said human body through driving said analgesic in depot sites in tissues under said transdermal analgesic delivery system into the systemic circulation at faster rates by said heating.

7. The method of claim 1, wherein said heating said skin of said human body effectuates an increase in said rate of analgesic delivery to said systemic circulation of said human body through increasing circulation of body fluid in tissues proximate said transdermal analgesic deliver system by said heating.

8. The method of claim 1, wherein said applying said temperature modification apparatus proximate said transdermal administered analgesic comprises applying said temperature modification apparatus proximate said temperature when breakthrough pain occurs.

9. The method of claim 8, further including discontinuing temperature adjustment when said breakthrough pain diminishes.

10. The method of claim 1, further including discontinuing said heating of said skin of said human body with said temperature modification apparatus when a desired clinical effect in said human body is achieved.

11. The method of claim 1, further including removing said temperature modification apparatus when a desired clinical effect in said human body is achieved.

12. The method of claim 1, further including terminating said heating said skin with a heat termination mechanism after a pre-determined duration of time.

* * * * *

UNITED STATES PATENT AND TRADEMARK OFFICE
CERTIFICATE OF CORRECTION

PATENT NO.    : 6,284,266 B1                                       Page 1 of 1
DATED         : September 4, 2001
INVENTOR(S)   : Jie Zhang and Hao Zhang It is certified that error appears in the above-identified patent and that said Letters Patent is hereby corrected as shown below:

<u>Title page,</u>
Insert Item:

-- [62]                     Related U.S. Application Data
Division of U.S. application Ser. No. 09/162,890, filed Sep. 29, 1998, U.S. Pat. No. 6,245,347, which is a continuation-in-part of U.S. application Ser. No. 08/819, 880, filed Mar. 18, 1997, now U.S. Pat. No. 5,919,479, which is a division of U.S. application Ser. No. 08/508,463, filed Jul. 28, 1995, now U.S. Pat. No. 5,658,583, hereby incorporated herein by reference. --

Signed and Sealed this

Twenty-fourth Day of August, 2004

JON W. DUDAS
*Director of the United States Patent and Trademark Office*